(12) United States Patent
Fisas Verges

(10) Patent No.: US 10,993,905 B2
(45) Date of Patent: May 4, 2021

(54) COSMETIC COMPOSITIONS COMPRISING MAGNETOSOMES AND USES THEREOF

(71) Applicant: NATURA BISSE INTERNATIONAL S. A., Barcelona (ES)

(72) Inventor: Patricia Fisas Verges, Barcelona (ES)

(73) Assignee: NATURA BISSÉ INTERNATIONAL S.A., Barcelona (ES)

(*) Notice: Subject to any disclaimer, the term of this patent is extended or adjusted under 35 U.S.C. 154(b) by 0 days.

(21) Appl. No.: 14/402,823

(22) PCT Filed: May 20, 2013

(86) PCT No.: PCT/EP2013/060338
§ 371 (c)(1),
(2) Date: Nov. 21, 2014

(87) PCT Pub. No.: WO2013/174774
PCT Pub. Date: Nov. 28, 2013

(65) Prior Publication Data
US 2015/0150785 A1    Jun. 4, 2015

Related U.S. Application Data

(60) Provisional application No. 61/667,230, filed on Jul. 2, 2012.

(30) Foreign Application Priority Data

May 21, 2012  (EP) .................................... 12003971

(51) Int. Cl.
| | | |
|---|---|---|
| *A61K 8/99* | (2017.01) |
| *A61K 8/02* | (2006.01) |
| *A61Q 17/04* | (2006.01) |
| *A61K 9/00* | (2006.01) |
| *A61Q 19/08* | (2006.01) |
| *A61K 35/74* | (2015.01) |
| *A61K 9/50* | (2006.01) |
| *A61K 8/19* | (2006.01) |
| *A61K 36/886* | (2006.01) |
| *A61L 26/00* | (2006.01) |
| *A61L 31/14* | (2006.01) |
| *A61L 31/16* | (2006.01) |
| *A61L 15/42* | (2006.01) |

(52) U.S. Cl.
CPC .............. *A61K 8/99* (2013.01); *A61K 8/0241* (2013.01); *A61K 8/19* (2013.01); *A61K 9/0009* (2013.01); *A61K 9/5094* (2013.01); *A61K 35/74* (2013.01); *A61K 36/886* (2013.01); *A61L 15/42* (2013.01); *A61L 26/0061* (2013.01); *A61L 31/14* (2013.01); *A61L 31/16* (2013.01); *A61Q 17/04* (2013.01); *A61Q 19/08* (2013.01); *A61K 2800/413* (2013.01); *A61K 2800/47* (2013.01); *A61L 2300/624* (2013.01); *A61L 2430/34* (2013.01)

(58) Field of Classification Search
CPC ........ A61K 8/99; A61K 8/0241; A61K 35/74; A61K 9/0009; A61K 9/5094; A61K 8/19; A61K 36/886; A61K 2800/47; A61K 2800/413; A61Q 19/08; A61Q 17/04; A61L 26/0061; A61L 31/14; A61L 31/16; A61L 15/42; A61L 2430/34
See application file for complete search history.

(56) References Cited

U.S. PATENT DOCUMENTS

| | | |
|---|---|---|
| 4,224,179 A | 9/1980 | Schneider |
| 4,385,119 A | 5/1983 | Blakemore |
| 6,074,385 A | 6/2000 | Klopotek |
| 6,083,539 A | 7/2000 | Yamada et al. |
| 6,251,365 B1 | 6/2001 | Bauerlein et al. |
| 2006/0051382 A1 | 3/2006 | Vidal |
| 2007/0148105 A1 | 6/2007 | Spector |
| 2010/0233219 A1 | 9/2010 | Aimi et al. |

FOREIGN PATENT DOCUMENTS

| | | |
|---|---|---|
| ES | 2192328 | 1/2000 |
| JP | 2011241194 A | 12/2011 |
| WO | 199840049 A2 | 9/1998 |
| WO | 2004000244 | 12/2003 |
| WO | 2006113227 A2 | 10/2006 |
| WO | 2006119102 | 11/2006 |
| WO | 2007/002047 | 1/2007 |
| WO | 20080040516 A2 | 4/2008 |
| WO | 2011061259 A1 | 5/2011 |
| WO | 2011147926 | 12/2011 |
| WO | 2012123925 A1 | 9/2012 |

OTHER PUBLICATIONS

Magnetosomes Are Cell Membrane Invaginations Organized by the Actin-Like Protein MamK: retrieved from internet:http://www.sciencemag.org/content/311/5758/242.short. Retrieved on Jul. 24, 2015.*
Aging in Elderly: Chronological Versus Photoaging: retrieved from internet: http://www.ncbi.nlm.nih.gov/pmc/articles/PMC3482795/. Retrieved on Dec. 30, 2015.*
K3129: retrieved from internet: http://www.sigmaaldrich.com/technical-documents/protocols/biology/vitamin-mixtures.html. Retrieved on Dec. 30, 2015.*
Sunburn: retrieved from internet: http://www.mayoclinic.org/diseases-conditions/sunburn/basics/complications/con-20031065. Retrieved on Oct. 5, 2016.*
Sun et al., "High-yield growth and magnetosome formation by Magnetospirillum gryphiswaldense MSR-1 in an oxygen-controlled fermentor supplied solely with air", Applied Microbiology Biotechnology, 2008, vol. 79, pp. 389-397.

(Continued)

Primary Examiner — Hong Yu
(74) Attorney, Agent, or Firm — Timothy H. Van Dyke; Wolter Van Dyke Davis, PLLC

(57) ABSTRACT

The present invention relates to cosmetic and skin care compositions comprising magnetosomes. The invention also relates to methods for the treatment of diseases associated with increased proliferation or accumulation of differentiating keratinocytes.

8 Claims, No Drawings

(56) References Cited

OTHER PUBLICATIONS

Qi et al., "Fur in Magnetospirillum gryphiswaldense Influences Magnetosomes Formation and Directly Regulates the Genes Involved in Iron and Oxygen Metabolism", PLOS One, 2012, vol. 7(1), e29572.

Schuler, D. et al., "A simple light scattering method to assay magnetism in Magnetospirillum gryphiswaldense", FEMS Microbiol. Lett., 1995, vol. 132, pp. 139-145.

Heyen, U et al., "Growth and magnetosome formation by microaerophilic Magnetospirillum strains in an oxygen-controlled fermentor", Appl. Microbiol. Biotechnol., 2003, vol. 61, pp. 536-544.

Komeili, A., "Molecular Mechanisms of Magnetosome Formation", Ann. Rev. Biochem., 2007, vol. 76, pp. 351-366.

Staniland, S. et al., "Controlled cobalt doping of magnetosomes in vivo", Nature Nanotech., 2008, vol. 3, pp. 158-162.

Franco, A., et al., "Temperature dependence of magnetic anisotropy in nanoparticles of $CoxFe(3x)O4$", J. Mag. Mag. Mat., 2008, vol. 320, pp. 709-713.

Tackett, R. et al., "Magnetic and optical response of tuning the magnetocrystalline anisotropy in $Fe3O4$ nanoparticle ferrofluids by Co doping", J. Mag. Mag Mat., 2008, vol. 320, pp. 2755-2759.

Wilder, L., et al., "Highly Potent Geminal Bisphosphonates. From Pamidronate Disodium (Aredia) to Zoledronic Acid (Zometa)", J. Med. Chem., 2002, vol. 45, pp. 3721-3728.

Neves, M., "Synthesis, characterization and biodistribution of bisphosphonates Sm-153 complexes: correlation with molecular modeling interaction studies", N. Med. Biol., 2002, vol. 29, pp. 329-338.

Shinoda, H. et al., "Structure-Activity Relationships of Various Bisphosphonates", Calcif. Tissue Int., 1983, vol. 35, pp. 87-89.

Merrel, M. A., "Inhibition of the mevalonate pathway and activation of p38 MAP kinase are independently regulated by nitrogen-containing bisphosphonates in breast cancer cells", Eur. J. Phramacol., 2007, vol. 570, pp. 27-37.

Mayer et al., "Techniques for Encapsulating Bioactive Agents Into Liposomes", Chemistry and Physics of Lipids, 1986, vol. 40, pp. 333-345.

Rostovtsev et al., "A Stepwise Huisgen Cycloaddition Process: Copper( )-Catalyzed Regioselective ™Ligationʃ of Azides and Terminal Alkynes", Angew, Chem. Int. Ed., 2002, vol. 41, pp. 2596-2599.

Tornoe et al., "Peptidotriazoles on Solid Phase: [1,2,3]-Triazoles by Regiospecific Copper(I)-Catalyzed 1,3-Dipolar Cycloadditions of Terminal Alkynes to Azides", Org. Chem., 2002, vol. 67, pp. 3057-3064.

Baskin et al., "Copper-free click chemistry for dynamic in vivo imaging", PNAS, 2007, vol. 104, No. 43, pp. 167393-167397.

Lin et al., "Mechanistic Investigation of the Staudinger Ligation", Am. Chem. Soc., 2005, vol. 127, pp. 2686-2695.

Saxon et al., "Cell Surface Engineering by a Modiped Staudinger Reaction", Science, Mar. 2000, vol. 287(5460), pp. 2007-2010.

Casey, "Development of the Olefin Metathesis Method in Organic Synthesis", Chem. Edu., 2006, vol. 83, No. 2, pp. 192-195.

Lynn et al., "Water-Soluble Ruthenium Alkylidenes: Synthesis, Characterization, and Application to Olefin Metathesis in Protic Solvents", Am. Chem. Soc., 2000, vol. 122, pp. 6601-6609.

Chen et al., "Advances of Olef in Polymerization in Aqueous Solutions", Progress in Chemistry, 2003, vol. 15, pp. 401-408.

Loh et al., ""Click" synthesis of small molecule-peptide conjugates for organellespecific delivery and inhibition of lysosomal cysteine proteases", Chem Commun (Camb), Nov. 2010, vol. 46(44), pp. 8407-8409.

Thomson, S., "Small-Molecule—Protein Conjugation Procedures", Methods Mol Med., 2004, vol. 94, pp. 255-265.

Zioni et al., "Strontium hexaferrite nanomagnets suspended in a cosmetic preparation: a convenient tool to evaluate the biological effects of surface magnetism on human skin", Skin Res. Technol., 2010, vol. 16, pp. 316-324, abstract only.

Alphandery E, et al, "Chains of magnetosomes extracted from AMB-1 magnetotactic bacteria for application in alternative magnetic field cancer therapy", ACSNano, vol. 5, Issue 8, pp. 6279-6296 (2011).

Das R, et al, "Current concepts in the pathogenesis of psoriasis", Indian J Dermatol, vol. 54, pp. 7-12 (2009).

Engin K, et al, "Hyperthermia and radiation in advanced malignant melanoma", Int. J Radiation Oncology Biol Phys., vol. 25, pp. 87-94 (1993).

Jeremy A, et al, "Inflammatory events are involved in acne lesion initiation", Acne Lesion Initiation, vol. 121, pp. 1-8 (2003).

Sun J, et al, "Bacterial magnetosome: a novel biogenetic magnetic targeted drug carrier with potential multifunctions", J Nanomaterials, pp. 1-13 (2011).

\* cited by examiner

COSMETIC COMPOSITIONS COMPRISING MAGNETOSOMES AND USES THEREOF

FIELD OF THE INVENTION

The present invention relates to compositions, preferably cosmetic or dermatological compositions, comprising a combination of active agents for combating the cutaneous signs of ageing, and in particular combating wrinkled skin and/or sagging skin.

BACKGROUND OF THE INVENTION

The concern to preserve for as long as possible a young-looking skin is a preoccupation of the majority of women and is also increasingly affecting the men. In order to meet this expectation, cosmetic compositions aimed at preventing and/or treating the signs of skin ageing have therefore been developed.

Skin aging is defined by all the alterations of the cutaneous covering resulting from the accumulation over the years of the gradual modifications of its various constituents.

It results, inter alia, in a flattening of the epidermis and of the dermo-epidermal junction and in the dermis, through, on the one hand, an overall reduction in the extracellular matrix (ECM) associated with a gradual decrease in collagen and elastin fibre production by fibroblasts and, on the other hand, by an increase in the destruction of these macromolecules by specific enzymes.

These biological phenomena therefore result in the induction, in the skin, of considerable physical modifications: loss of firmness, sagging. The skin loses its elasticity and the features slacken. The slackening of the subcutaneous tissues (fats and muscles) leads to an excess of skin and ptosis. This slackening is characterized by drooping of the cheekbones and of the cheeks, entraining the lower eyelid. Associated with surface mechanical stress, wrinkles form then accentuate and become deeper. In addition, during the day, depending on water movement due to gravity, some wrinkles increase and become more marked.

Among the wrinkles that coexist on the face, it is thus possible to make a distinction between embryonic wrinkles which are derived from small starting points invisible to the naked eye, which join up together over time to form a wrinkle; deeper marked wrinkles, resulting from the hollowing of certain furrows over time; and reversible wrinkles, which originate from the decrease over the day in the thickness of the skin and in the increase in its elasticity.

A certain number of compounds have already been identified as anti-wrinkle active agents and used in cosmetic compositions for the purposes of combating the cutaneous signs of ageing, and in particular decreasing and/or smoothing out skin wrinkles.

For example, retinol has a certain efficacy as an anti-wrinkle active agent, in particular by virtue of its anti-differentiating properties. However, retinol is an active agent which only acts long term. Moreover, in order to ensure tolerance in cosmetics, the amount of retinol introduced into cosmetic compositions is restricted, thereby limiting its effectiveness.

The invention aims precisely to compensate for this insufficiency, and makes it possible in particular to accelerate the manifestation of a visible effect on the reducing and/or smoothing out of skin wrinkles.

SUMMARY OF THE INVENTION

In a first aspect, the invention relates to a cosmetic or skin care composition comprising magnetosomes and a cosmetically acceptable adjuvant, wherein the magnetosomes are isolated from a magnetotactic microorganism and wherein the cosmetically acceptable adjuvant is selected from the group consisting of fillers, UVA and/or UVB sunscreens, thixotropic agents, antioxidants, dyes, pigments, fragrances, thickeners, vitamins, moisturizers, and nonionic or amphoteric polymers.

In a second aspect, the invention relates to a cosmetic method for skin care in a subject which comprises the topical administration to said subject of a composition comprising magnetic nanoparticles which are forming part of a magnetosome, wherein the nanoparticles have not been placed in a magnetic field prior to administration and/or wherein the nanoparticles are not subjected to a magnetic field after application, wherein the magnetosomes are isolated from a magnetotactic microorganism.

In another aspect, the invention relates to a composition comprising magnetic nanoparticles for use in the treatment of a disease which is associated with increased proliferation or accumulation of differentiating keratinocytes, of a disease which requires increased proliferation of keratinocyte progenitors or for wound healing, wherein the magnetic particles are forming part of a magnetosome and wherein the magnetosomes are isolated from a magnetotactic microorganism.

In another aspect, the invention relates to a cosmetic or skin care composition comprising magnetosomes and a cosmetically acceptable adjuvant wherein the magnetosomes contain an effective amount of at least a cosmetically active agent which is bound to the magnetosomes or incorporated into the magnetosomes, wherein the magnetosomes are isolated from a magnetotactic microorganism.

In another aspect, the invention relates to a cosmetic method for skin care in a subject comprising the topical administration to said subject of the cosmetic or skin care composition according to the invention and applying a magnetic field under conditions adequate for the release of the cosmetically active agent from the magnetosomes.

DETAILED DESCRIPTION OF THE INVENTION

Definition of Terms

The term "actinic keratosis" as used herein, includes solar or senile keratosis and refers to very common bening tumor lesions triggered by different intrinsic and extrinsic factor (i.e. age or sun exposure). They are caused in many cases by an excessive proliferation of suprabasal keratinocytes which results in a hyperkeratinized lesion with scar appearance.

As used herein, the term "allantoin" refers to the chemical compound (2,5-Dioxo-4-imidazolidinyl) urea. Allantoin is the product of oxidation of uric acid by purine catabolism in most mammals, excluding humans and higher apes.

The term "agent for treating perspiration" means any substance which, by itself, has the effect of reducing the sensation on the skin of moisture associated with human sweat, or of masking human sweat. Antiperspirant actives for use herein are often selected from astringent active salts, including in particular astringent aluminium, zirconium and mixed aluminium/zirconium salts, including both inorganic salts, salts with organic anions and complexes. Preferred astringent salts include aluminium, zirconium and aluminium/zirconium halohydrate salts, and especially chlorohydrates. Aluminium/zirconium chlorohydrates complexed with glycine are particularly desirable antiperspirant actives in stick compositions herein.

The term "anti-acne active agent" especially means any active agent that has effects on the specific flora of greasy skin, for instance *Propionibacterium acnes* (*P. acnes*). These effects may be bactericidal. Suitable anti-acne agents can be drying agents, keratolytic agents, epidermolytic agents, anti-microbial agents and retinoids. Examples of anti-acne agents include sulfur, resorcinol, glycolic acid, lactic acid, pyruvic acid, salicylic acid, retinoic acid, derivatives of retinoic acid, and antimicrobial agents, e.g., benzoyl peroxide, erythromycin, triclosan, azelaic acid, clindamycin, chlorhexidine, neomycin, miconazole, clotrimazole and tetracycline.

The term "amino acid", as used herein, refers to a molecule containing an amine group, a carboxylic acid group, and a side-chain that is specific to each amino acid. The term includes naturally occurring as well as synthetic amino acids, as well as amino acid analogs and amino acid mimetics that function in a manner similar to the naturally occurring amino acids.

As used herein, the term "anti-inflammatory agent" refers to the property of a substance or composition in reducing acute and/or chronic inflammatory responses, and/or in preventing or treating an inflammatory-related disease. Anti-inflammatory activity" herein means activity as determined by any generally accepted in vitro or in vivo assay or test, for example an assay or test for inhibition of prostaglandin production or cyclooxygenase activity. Anti-inflammatory agents include steroidal anti-inflammatory agents, non-steroidal anti-inflammatory agents and "natural" anti-inflammatory agents. Steroidal anti-inflammatory agents include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.
Specific non-steroidal anti-inflammatory agents useful in the composition invention include, but are not limited to
1) the oxicams, such as piroxicam, isoxicam, tenoxicam, sudoxicam, and CP-14,304; 2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;
4) the fenamates, such as mefenamic, meclofenamic, flufenamic, niflumic, and tolfenamic acids;
5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and
6) the pyrazoles, such as phenylbutazone, oxyphenbutazone, feprazone, azapropazone, and trimethazone.

Mixtures of these non-steroidal anti-inflammatory agents may also be employed, as well as the dermatologically acceptable salts and esters of these agents.

Finally, so-called "natural" anti-inflammatory agents are useful in methods of the present invention. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), *aloe vera*, plant sterols (e.g., phytosterol), Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, and sea whip extract, may be used.

Additional anti-inflammatory agents useful herein include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include C2-C24 saturated or unsaturated esters of the acids, preferably C10-C24, more preferably C16-C24.

As used herein, the term "antioxidant" means any cosmetically acceptable substance which delays, retards or prevents the decay or deterioration of components of the cosmetic composition due to oxidation as well as a substance which prevent oxidation of the cellular components of the skin. Examples of antioxidants include, but are not limited to, water-soluble antioxidants such as sulfhydryl compounds and their derivatives (e.g., sodium metabisulfite and N-acetyl-cysteine, glutathione), lipoic acid and dihydrolipoic acid, stilbenoids such as resveratrol and derivatives, lactoferrin, iron and copper chelators and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, vitamin E (i.e., tocopherols such as alpha-tocopherol), derivatives of vitamin E (e.g., tocopheryl acetate), retinoids such as retinoic acid, retinol, trans-retinol, cis-retinol, mixtures of trans-retinol and cis-retinol, 3-dehydroretinol and derivatives of vitamin A (e.g., retinyl acetate, retinal and retinyl palmitate, also known as tetinyl palmitate), butylated hydroxytoluene, tocotrienols, and ubiquinones. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, black tea, white tea, pine bark, feverfew, parthenolide-free feverfew, oat extracts, blackberry extract, cotinus extract, soy extract, pomelo extract, wheat germ extract, Hesperedin, Grape extract, *Portulaca* extract, Licochalcone, chalcone, 2,2'-dihydroxy chalcone, *Primula* extract, propolis, and the like. Also comprised are agents capable of inducing an increase in the levels or activity of Glutathione or intracellular antioxidant enzymes (catalase, superoxide simutase, etc.).

As meant herein, the term "betaine" is used in its meaning of glycine betaine or N,N,N-trimethylglycine, a zwitterion found a.o. in sugar beets (*Beta vulgaris*).

As used herein, "collagen" refers to a protein of connective tissue in animals characterised in that is formed by a regular arrangement of amino acids in each of the three chains of these collagen subunits. The sequence can often follow the pattern Gly-Pro-Y or Gly-X-Hyp, where X and Y can be any of various other amino acid residues, and Hyp is hydroxyproline. Collagen can refer to any one of the known collagen types, including known collagen types, such as collagen types I through XIX, as well as to any other collagens, whether natural, synthetic, semi-synthetic, or recombinant. The term "collagen" can also encompass pro-collagens. The term "collagen" specifically encompasses variants and fragments thereof, and functional equivalents and derivatives thereof, which preferably retain at least one structural or functional characteristic of collagen.

The term "conjugated," as used herein with respect to the relationship of a first moiety to a second moiety, e.g., the conjugation of a cosmetically active agent to a magnetic nanoparticle, refers to the formation of a covalent bond between a first moiety and a second moiety. In the same context, "conjugated" refers to the covalent bond. The conjugation can be a direct conjugation, e.g., through a direct bond of the first moiety to the second moiety, or can be through a linker (e.g., through a covalently linked chain of one or more atoms disposed between the first and second moiety). E.g., where an attachment is through a linker, a first moiety (e.g., a cosmetically active agent) is covalently bonded to a linker, which in turn is covalently bonded to a second moiety (e.g., the magnetic nanoparticle).

The term "cosmetically active agent", as used herein, refers to a compound (e.g., a synthetic compound or a compound isolated from a natural source or a natural extract) that has a cosmetic or therapeutic effect on the skin or hair, including, but not limiting to, anti-acne agents, shine control agents, anti-mycotic agents, anti-parasite agents, external analgesics, sunscreens, photoprotectors, antioxidants, keratolytic agents, surfactants, moisturizers, vitamins, energy enhancers, anti-perspiration agents, astringents, deodorants, anti-callous agents, and agents for hair and/or skin conditioning.

The term "cosmetic composition" as used herein refers in particular to cosmetic compositions that can be topically applied to mammalian keratinous tissue such as e.g. human skin or scalp. The term "cosmetic composition" as used in the present application refers to cosmetic compositions as defined under the heading "Kosmetika" in Rompp Lexikon Chemie, 10th edition 1997, Georg Thieme Verlag Stuttgart, New York as well as to cosmetic compositions as disclosed in A. Domsch, "Cosmetic Compositions", Verlag für chemische Industrie (ed. H. Ziolkowsky), 4th edition, 1992.

As used herein, the term "cosmetically acceptable" modifying a substance means that the substance is of sufficiently high purity and suitable for use in contact with human skin without undue toxicity, incompatibility and instability. A "cosmetically acceptable" substance, preferably, causes little or no allergic response.

As used herein, the term "differentiating keratinocytes" refers to those keratinocytes which are found in the stratum *granulosum* and stratum *spinosum* of the skin.

The term "deodorant" refers to any substance that is capable of masking, absorbing, improving and/or reducing the unpleasant odour resulting from the decomposition of human sweat by bacteria.

The terms "dye" and "pigment" are used herein indistinctly to refer to an active agent capable of colorizing fibers, hair and other materials which are used either to provide a certain color to the formula or to counteract the color certain skin pigmentations/spots achieving a visual effect. Suitable dyes include natural dyes, which is understood to mean any dye or dye precursor which occurs naturally and which is produced either by extraction (and optionally purification) from a plant matrix or artificial dyes which are obtained by chemical synthesis. Suitable natural dyes suitable in particular for the implementation of the invention can be chosen, for example, from carminic acid, kermesic acid, isatin, chlorophyllins, hematein, hematoxylin, brazilin, beta-carotene, brazilein, betanin, flavonoids or anthocyanins.

The term "effective amount" of pharmacologically active agent or cosmetic agent refers to a substantially nontoxic but sufficient amount of a compound to provide the desired effect and performance at a reasonable benefit/risk ratio attending any medical or cosmetic treatment.

The term "embed," as used herein, refers to the formation of a non-covalent interaction between a first moiety and a second moiety, e.g., a cosmetically active agent and a magnetic nanoparticle. An embedded moiety, e.g., a cosmetically active agent embedded particle, is associated with the particle through one or more non-covalent interactions such as van der Waals interactions, hydrophobic interactions, hydrogen bonding, dipole-dipole interactions, ionic interactions, and pi stacking. An embedded moiety has no covalent linkage to the particle in which it is embedded. An embedded moiety may be completely or partially surrounded by particle in which it is embedded.

As used herein, an "emollient" is a compound that helps to maintain the soft, smooth, and pliable appearance of the skin (e.g., by remaining on the skin surface or in the stratum corneum to act as a lubricant). Examples of suitable emollients include those found in Chapter 35, pages 399-415 (Skin Feel Agents, by G Zocchi) in Handbook of Cosmetic Science and Technology (edited by A. Barel, M. Paye and H. Maibach, Published in 2001 by Marcel Dekker, Inc New York, N.Y.), and include, but are not limited to, petrolatum, hexyldecyl stearate and plant, nut, and vegetable oils such as macadamia nut oil, rice bran oil, grape seed oil, palm oil, prim rose oil, hydrogenates peanut oil, and avocado oil.

As used herein an "energy enhancer" is a compound which stimulates cellular metabolism. Energy enhancers include, for example, vitamins of the vitamin B group, creatine, choline, and some branched chain amino acids. Vitamins of the vitamin B group include, for example, vitamin B1 (thiamine, aneurin), vitamin B2 (riboflavin), vitamin PP (niacinamide), vitamin B6 (pyridoxine), pantothenic acid, and L-camitine.

The term "epidermolytic ichthyosis", as used herein, refers to a form of ichthyosis which is caused by the presence of abnormal Keratin 1 and Keratin 10 in the uppermost layers of the skin, which results in the abnormal aggregation of keratin filaments and hyperkeratinization.

The term "filler" should be understood as meaning a colorless or white, inorganic or synthetic particle which is insoluble in a possible liquid component in the composition according to the present invention, whatever the temperature at which the composition is manufactured. The filler can be inorganic or organic, and can be of spherical or oblong shape, whatever the crystallographic form (for example, sheet, cubic, hexagonal, orthorhombic, and the like). Non-limiting mention may be made of talc, mica, silica, kaolin, sericite, calcinated talc, calcinated mica, calcinated sericite, synthetic mica, bismuth oxychloride, barium sulfate, boron nitride, calcium carbonate, magnesium carbonate, magnesium hydrogen carbonate and hydroxyapatite, in particular calcium hydroxyapatitie, powders formed of polyamide (Nylon®), of poly-alanine and of polyethylene, powders formed of polyurethane, powders formed of tetrafluoroethylene polymers (Teflon®), lauryllysine, starch, polymeric hollow microspheres, such as those of poly (vinylidene chloride)/acrylonitrile, for example Expancel® (Nobel Industrie), of acrylic acid copolymers, such as Polymethylmethacrylate, silicone resin microbeads (Tospearls® from Toshiba, for example), collagen, hyaluronic acid, polylactic acid, particles formed of polyorganosiloxane elastomers, precipitated calcium carbonate, magnesium carbonate, basic magnesium carbonate, hollow silica microspheres, glass or ceramic microcapsules, or metal soaps derived from organic carboxylic acids having from 8 to 22 carbon atoms, such as from 12 to 18 carbon atoms, for example zinc stearate, magnesium stearate, lithium stearate, zinc laurate or magnesium myristate.

The term "fragrance" is meant to encompass any component reacting with the human olfactory sites and imparting a pleasurable odor, essence or scent.

The term "follicular hyperkeratosis" is used herein indistinctly with the term phrynoderma and is used to refer to an hereditary common mild condition caused by overproduction of keratin inside the hair follicles with plugged follicles full of protein, sebum, debris and associated inflammation as a result.

The term "growth factor" can be a naturally occurring, endogenous or exogenous protein, or recombinant protein, capable of stimulating cellular proliferation and/or cellular differentiation and cellular migration. Growth factors include but are not limited to fibroblast growth factor (FGF), platelet-derived growth factor (PDGF), insulin-like growth factors (IGF) I and II, TGF-beta, TGF-alpha, bone morphogenetic protein (BMP) (e.g., BMP-2, BMP-3, BMP-4, BMP-6, or BMP-7), hedgehog proteins, growth differentiation factors, hematopoietic colony-stimulating factors (CSF), vascular endothelium growth factor (VEGF), osteoid-inducing factor (OIF), angiogenins, endothelins, hepatocyte growth factor, keratinocyte growth factor, ADMP-1, interleukins (IL) (e.g., IL-3 and IL-6), epithelial growth factors, dexamethasone, leptin, sortilin, transglutaminase, prostaglandin E, 1,25-dihydroxyvitamin D3, ascorbic acid, procollagen, glycerol phosphate, TAK-778, statins, growth hormone, steel factor (SF), activin A (ACT), retinoic acid (RA), epidermal growth factor (EGF), hematopoietic growth factors, peptide growth factors, erythropoietin, tumor necrosis factors (TNF), interferons (IFN), heparin binding growth factor (HBGF), nerve growth factor (NGF) and muscle morphogenic factor (MMP).

The term "hormone" as used herein refers to natural substances produced by organs of the body that travel by blood to trigger activity in other locations as well as their synthetic analogs that mimic (at least partially) the beneficial action of certain human hormones in the skin, such as isoflavones.

The terms "humectant", "moisturizer" and "wetting agent" are used herein indistinctly to refer to a compound intended to increase the water content of the top layers of skin (e.g., hygroscopic compounds). Examples of suitable humectants include those found Chapter 35, pages 399-415 (Skin Feel Agents, by G Zocchi) in Handbook of Cosmetic Science and Technology (edited by A. Barel, M. Paye and H. Maibach, Published in 2001 by Marcel Dekker, Inc New York, N.Y.) and include, but are not limited to, glycerin, sorbitol or trehalose (e.g., α,α-trehalose, β,β-trehalose, α,β-trehalose), salt or ester thereof (e.g., trehalose 6-phosphate), urea; guanidine; *aloe vera*; glycolic acid and glycolate salts such as ammonium and quaternary alkyl ammonium; lactic acid and lactate salts such as sodium lactate, ammonium lactate and quaternary alkyl ammonium lactate; polyhydroxy alcohols such as sorbitol, glycerol, hexanetriol, propylene glycol, butylene glycol, hexylene glycol, polyethylene glycol; carbohydrates such as alkoxylated glucose; starches; starch derivatives; glycerin; pyrrolidone carboxylic acid (PCA); lactamide monoethanolamine; acetamide monoethanolamine; volatile silicone oils; nonvolatile silicone oils; and mixtures thereof. Suitable silicone oils can be polydialkylsiloxanes, polydiarylsiloxanes, polyalkarylsiloxanes and cyclomethicones having 3 to 9 silicon atoms.

The term "hyperkeratosis", as used herein, refers to a disease characterized by excessive cornification of skin areas.

The term "ichthyosis", as used herein, refers any skin disease characterized by extremely dry, scaly skin, with hyperthickened stratum corneum.

The term "ichthyosis *hystrix* (Curth-Macklin type)", as used herein, refers to a rare skin disorder characterized by verrucous or spin-like brown-grey massive hyperkeratosis that can be caused by abnormal Keratin 1.

The term "ichtyosis *vulgaris*" refers to a mild form of ichthyosis which is caused by the presence of an abnormal (mutant) form of Filaggrin in the skin.

As used herein, "individual" indicates an animal, preferably a mammal, including humans, primates, laboratory animals (e.g. rats, mice, etc.), farm animals (e.g. cows, sheep, goats, pigs, etc.), pets (e.g. dogs, cats, etc.), and sport animals (e.g. horses, etc.). In some embodiments, an individual is a human. Reference to "about" a value or parameter herein also includes (and describes) embodiments that are directed to that value or parameter per se.

The term "keratolytic" refers to substances capable of facilitating the elimination of dead cells of the horny layer of the epithelium, such as for example salicylamide, salicylic acid, tamarind (tamarindus indica) or enzymes. Examples of useful keratolytic and/or desquamating agents include urea, salicylic acid and alkyl derivatives thereof, saturated and unsaturated monocarboxylic acids, saturated and unsaturated bicarboxylic acids, tricarboxylic acids, alpha hydroxyacids and beta hydroxyacids of monocarboxylic acids, alpha hydroxyacids and beta hydroxyacids of bicarboxylic acids, alpha hydroxyacids and beta hydroxyacids of tricarboxylic acids, ketoacids, alpha ketoacids, beta ketoacids, of the polycarboxylic acids, of the polyhydroxy monocarboxylic acids, of the polyhydroxy bicarboxylic acids, of the polyhydroxy tricarboxylic acids.

The term "keratinocyte", as used herein, refers to the cells which form the predominant cell type in the epidermis characterized by the presence of a number of structural proteins (filaggrin, keratin), enzymes (proteases), lipids and antimicrobial peptides (defensins) which contribute to maintain the important barrier function of the skin.

The term "keratinopathic ichthyosis disease", as used herein, refers to ichthyosis conditions caused by defects in Keratin 1, Keratin 2 and Keratin 10 genes.

A "lubricant" is understood as a substance which, when placed between two mobile parts, forms a film preventing the contact thereof, thereby preventing the friction or appearance of unwanted force components and therefore a more physiological tooth movement anti-perspiration agents.

The phrase "magnetic field" as used herein means a condition that is generally found in the region(s) around a magnet or an electric current, characterized by the existence of a detectable magnetic force, typically at every point in the region, and by the existence, of magnetic poles. A magnetic field is that part of an electromagnetic field that exerts a force on a moving charge. A magnetic field can be caused either by another moving charge (i.e., by an electric current) or by a changing electric field. Generators of magnetic field can be represented by permanent magnets, electromagnets single or multiplex and any their combination and/or configuration. The magnetic field is usually defined in many equivalent ways based on the effects it has on its environment. For instance, a particle having an electric charge, q, and moving in a magnetic field with a velocity, v, experiences a force, F, called the Lorentz force. Alternatively, the magnetic field can be defined in terms of the torque it produces on a magnetic dipole.

The term "magnetosome", as used herein, refers to magnetic nanoparticles and which further contain a membrane which surrounds them. The membrane can be a synthetic membrane of defined composition as well as a membrane derived from a magnetotactic microorganism (including the lipids of said microorganism as well as the specific membrane-associated polypeptides which appear in the magnetosome). Preferably, the magnetic nanoparticles are iron oxide nanoparticles made of magnetite ($Fe_3O_4$), iron sulfide (greigite or $Fe_3S_4$) or mixtures thereof. The magnetite found in the magnetosomes can become oxidized to maghemite after extraction from the bacteria. Therefore, magnetosomes may contain mixtures of magnetite and maghemite. The term magnetosomes refers to chains of magnetosomes as they are usually arranged within the bacteria as well as to individual magnetosomes.

The term "magnetotactic microorganism", as used herein, refers to any microorganism which is capable of synthesizing iron-rich particles, which may be arranged in chains of five to ten particles apiece. The presence of this particles confers the microorganism with a permanent ferromagnetic dipole moment which results in that this microorganisms are capable of orienting in a preferred direction relative to the geomagnetic field. Suitable magnetotactic microorganisms that can be used in the present invention include, without limitation, *Magnetospirillum gryphiswaldense* MSR-1, *Magnetospirillum magneticum* AMB-1, *Magnetospirillum magnetotacticum* MS-1, *Magnetospirillum magneticum* strain MGT-1, magnetotactic coccus strain MC-1, *Desulfovibrio magneticus* RS-1 and anaerobic *vibrio* strains MV-1, MV-2 and MV-4. Suitable methods for determining whether a microorganism is magnetotactic include, without limitation, by determining the total cellular iron content by atom absorption spectrophotometry as described by Suzuki T. et al (FEBS Lett., 2007, 581: 3443-3448), by determining the yield of magnetosomes using magnetic separation of an extract of the microorganism followed by fractionation of the bound fraction using isopicnic centrifugation in a density gradient as described by Grünberg et al. (Appl Microbiol Biotechnol., 2008 79:389-397), by inspecting the microorganism by transmission electron microscopy as described by Qi et al. (PLoS One. 2012; 7(1):e29572) or by light scattering as described by Schüler D. et al (FEMS Microbiol Lett, 1995, 132: 139-145).

As used herein, the term "magnetic nanoparticle" is meant to include any nanoparticle which moves in response to being placed in an appropriate magnetic field. This term is meant to also include ferromagnetic, paramagnetic and diamagnetic materials. Non-limiting suitable examples can include, $Fe_2O_3$, $Fe_3O_4$, $Fe_2O_4$, FexPty, CoxPty, MnFexOy, CoFexOy, NiFexOy, CuFexOy, ZaFexOy, and CdFexOy, wherein x and y vary between 1 and 6, depending on the method of synthesis known in the art.

As used herein, the term "maslinic acid" refers to a triterpenic compound of the group of oleanes which is derived from dry olive-pomace oil (an olive skin wax) which is a byproduct of olive oil extraction and which CAS accession number is 4373-41-5.

The term "melatonin" means 5-methoxy-N-acetyltryptamine and its derivatives or analogs that have substantially the same biological activity as 5-methoxy-N-acetyltryptamine, and their in vivo precursors.

The term "mucosa" relates to a non-damaged or damaged mucosa of an animal, such as a human, and can refer to the oral, mouth, aural, nasal, pulmonary, ocular, gastrointestinal, vaginal or rectal mucosa.

"Nanoparticle", as used herein, refers to a particle having a diameter ranging from about 1 to about 1000 nanometers. The nanoparticles for use according to the invention typically have an average particle diameter of less than 300 nm, preferably less than 200 nm and especially less than 100 nm In one embodiment, the nanoparticles have an average particle diameter in the range of from 10 to 100 nm, preferably from 20 to 80 nm and especially from 20 to 50 nm The average particle diameter is the average maximum particle dimension, it being understood that the particulars are not necessarily spherical The particle size may conveniently be measured using conventional techniques such as microscopy techniques for example scanning electron microscopy In one embodiment, the nanoparticles for use according to the invention have a spherical or substantially spherical shape The shape may conveniently be assessed by conventional light or electron microscopy techniques.

As used herein, a "nucleotide" is given its ordinary meaning as used in the art, i.e., a molecule comprising a sugar moiety, a phosphate group, and a base (usually nitrogenous). Typically, the nucleotide comprises one or more bases connected to a sugar-phosphate backbone (a base connected only to a sugar moiety, without the phosphate group, is a "nucleoside"). Suitable nucleotides include, without limitation, adenosine triphosphate (ATP), guanosine triphosphate (GTP), diguanosine tetraphosphate (DGTP) and the like.

The term "oligosaccharide", as used herein, are defined in the art as a molecule being composed of up to nine saccharide units (see, for example, Roberts, J. D., and Caserio, M. C., Basic Principles of Organic Chemistry (1964) p. 615). Representative examples include, without limitation, disaccharides such as, but not limited to, sucrose, maltose, lactose, and cellobiose; trisaccharides such as, but not limited to, mannotriose, raffinose and melezitose; and tetrasaccharides, such amylopectin, Syalyl Lewis X (SiaLex), and the like.

The term "palmoplantar keratodermas", as used herein, refers to an hereditary or acquired hyperkeratosis which occurs in the palms and soles.

The term "papulosquamous hyperkeratosis" as used herein, refers to excessive thickening of the stratum corneum resulting in papules and scales on the skin's surface); some examples are drug-induced keratoderma, granular parakeratosis (or axillary granular parakeratosis) or keratosis *punctata* of the palmar creases.

The term "plaque psoriasis", as used herein, refers to the most common type of psoriasis, which is an inflammatory condition of the skin characterized by scaly inflammatory plaques. It can be hereditary and there is a wide variety in the clinical symptoms as well as in the evolution of the disease depending on each individual.

The term "polysaccharide" as used herein is meant to include compounds composed of 10 saccharide units and up of hundreds and even thousands of monosaccharide units per molecule, which are held together by glycoside bonds and range in their molecular weights from around 5,000 and up to millions of Daltons. Examples of common polysaccharides include, but are not limited to starch, glycogen, cellulose, gum arabic, beta-glucans, agar and chitin.

The term "preserving agent" is understood to refer to any compound having antimicrobial and/or antioxidant action. Suitable preservatives include, for example, parabens, quaternary ammonium species, phenoxyethanol, benzoates, DMDM hydantoin, organic acids.

The term "skin" refers to the outer covering of an animal body; the outermost layer of skin is called the epidermis, the layer beneath the epidermis is called the dermis.

The term "skin care agent" refers to an agent that has one or more beneficial effects on the care and/or hygiene of the skin. It is to be understood that skin care active agents are useful not only for application to skin, but also to hair, scalp, nails and other mammalian keratinous tissue.

"Skin care composition", as used herein, refers to a cosmetic composition comprising one or more skin care agents.

A "shine control agent", as used herein, refers to products that improve and/or regulate the condition of the shiny appearance of skin. A frequent, undesirable condition is "oily skin", which results from the excessive amount of sebum and sweat that is excreted onto the skin. Sebum is an oily mixture, composed principally of squalene, triglycerides, fatty acids and wax esters. Sebum is produced in the sebaceous glands of the skin. Oily skin is associated with a shiny, undesirable appearance and disagreeable tactile sensation. Sweat is predominantly water with trace quantities of dissolved inorganic salts such as sodium chloride and potassium chloride. Typically, shine-control agents are porous in nature. These agents, when applied to the skin provide a reservoir to absorb excess moisture into the pores, hence reducing the visible quantity of moisture on the skin. Suitable shine-control agents include, but are not limited to, silicas, magnesium aluminum silicates, talc, sericite and various organic copolymers. Particularly effective shine control agents include silicates or carbonates that are formed by reaction of a carbonate or silicate with the alkali (IA) metals, alkaline earth (IIA) metals, or transition metals, and silicas (silicon dioxide). Shine control agents that may be used include calcium silicates, amorphous silicas, calcium carbonates, magnesium carbonates, zinc carbonates, and combinations thereof. Some specific examples of the silicates and carbonates useful in this present invention are more fully explained in Van Nostrand Reinhold's Encyclopedia of Chemistry, 4.sup.th Ed. pp 155, 169, 556, and 849 (1984).

"Signs of skin aging" include, but are not limited to, all outwardly visible or tactilely perceptible manifestations as well as any other macro or micro effects due to skin aging. Such signs may be induced or caused by intrinsic factors or extrinsic factors, e.g., chronological aging and/or environmental damage. These signs may result from processes that include, but are not limited to, the development of textural discontinuities such as wrinkles and coarse deep wrinkles, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including under eye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

The terms "smoothing" and "softening" as used herein mean altering the surface of the skin and/or keratinous tissue such that its tactile feel is improved.

The term "stem cells", as used herein, means those mammalian cells which maintain and repair the tissues in which they are found, including epidermal stem cells.

As used herein a "sunscreen" or "light protection filter" or "photoprotective composition" refers to a composition which is suitable for administration to an individual which provides protection against light irradiation (i.e. acts as a light or sun-absorbing compound), particularly of ultraviolet and visible light, preferably wavelength 280-700 nm, especially preferably at least 350-500 nm, e.g. 370-500 nm, 375-490 nm, 400-480 nm, 400-500 nm or 425-475 nm. Herein, suitable sunscreens include oil-soluble sunscreens, insoluble sunscreens, and water-soluble sunscreens. Non-limiting examples of suitable oil-soluble sunscreens include benzophenone-3, bis-ethylhexyloxyphenol methoxyphenyl triazine, butyl methoxydibenzoyl-methane, diethylamino hydroxy-benzoyl hexyl benzoate, drometrizole trisiloxane, ethylhexyl methoxy-cinnamate, ethylhexyl salicylate, ethylhexyl triazone, octocrylene, homosalate, polysilicone-15, and derivatives and mixtures thereof. Non-limiting examples of suitable insoluble sunscreens include methylene bis-benzotriazolyl tetramethylbutyl-phenol, titanium dioxide, zinc cerium oxide, zinc oxide, and derivatives and mixtures thereof. Non-limiting examples of suitable water-soluble sunscreens include phenylbenzimidazole sulfonic acid (PBSA), terephthalylidene dicamphor sulfonic acid, (Mexoryl™ SX), benzophenone-4, benzophenone-5, benzylidene camphor sulfonic acid, cinnamidopropyl-trimonium chloride, methoxycinnamido-propyl ethyldimonium chloride ether, disodium bisethylphenyl triaminotriazine stilbenedisulfonate, disodium distyrylbiphenyl disulfonate, disodium phenyl dibenzimidazole tetrasulfonate, methoxycinnamido-propyl hydroxysultaine, methoxycinnamido-propyl laurdimonium tosylate, PEG-25 PABA (p-aminobenzoic acid), polyquaternium-59, TEA-salicylate, and salts, derivatives and mixtures thereof.

As used herein, a "surfactant" is a surface-active agent intended to cleanse or emulsify. Examples of suitable surfactants include those found in Chapter 37, pages 431-450 (Classification of surfactants, by L. Oldenhove de Guertechin) in Handbook of Cosmetic Science and Technology (edited by A. Barel, M. Paye and H. Maibach, Published in 2001 by Marcel Dekker, Inc New York, N.Y.) Suitable surfactant/emulsifying agents include ceteareths, ceteths, laneths, laureths, isoseareths, steareths, cetyl alcohol, deceths, dodoxynols, glyceryl palmitate, glyceryl stearate, laneths, myreths, nonoxynols, octoxynols, oleths, PEG-castor oil, poloxamers (e.g., poloxamer 407), poloxamines, polysorbates, sodium laurate, ammonium laureth sulfate, sodium laureth sulfate, sodium lauroyl sarcosinate, sodium lauroyl taurate, sodium lauryl sulfate, sodium methyl cocoyl taurate, sodium methyl oleoyl taurate, sodium nonoxynol sulfate, sodium cetyl sulfate, sodium cetearyl sulfate, sodium cocoate, sodium cocoyl isethionate and sodium cocoyl sarcosinate. Other suitable surfactant/emulsifying agents would be known to one of skill in the art and are listed in the CTFA International Cosmetic Ingredient Dictionary and Handbook, Vol. 2, 7th Edition (1997). Preferred surfactants include octoxynol-9 and polysorbate-20.

The term "thixotropic material" refers to a material that has a certain viscosity in a resting state, but which changes viscosity in response to shear. Thixotropic material may take the form of solids, liquids, gases, and semi-solid materials. Examples of thixotropic materials include structured liquids, suspensions, emulsions, polymer solutions, aqueous iron oxide gels, vanadium pentoxide sols, starch pastes, pectin gels, flocculated paints, clays, soil suspensions, creams, drilling muds, flour doughs, flour suspensions, fibre greases, jellies, paints, honey, carbon-black suspensions, hydrophobically modified hydroxethyl cellulose, non-associative cellulose water solutions, flocculated polymer latex suspension, rubber solutions, metal slushes, bentonite clays, modified laponites, oils, lubricants, coal suspensions, xanthan gums, organic bentonite, fumed silica, aluminum stearate, metal soap, castor oil derivatives or thixotropic epoxy resin. The term should be taken to include thixotropic materials which show a time-dependent change in viscosity, i.e. the longer the fluid/material undergoes shear stress, the lower its viscosity. Many gels and colloids are thixotropic materials which exhibit a stable form at rest but become fluid when agitated.

As used herein, the term "thickening agent" generally refers to a substance used for regulating the viscosity of fluid (such as liquid, semi-solid, etc.), usually increasing the viscosity of fluid, and can also be referred to herein as a viscosity regulator. Thickeners may be either synthetic or natural. Thickeners may be used to gel or thicken cosmetic compositions to provide, for example, better deposition properties. Natural thickeners may include waxes, gums and powders and mixtures thereof. Natural waxes may include beeswax, carnauba, and/or candelilla and mixtures thereof. Natural gums may include *acacia*, xanthan, schelortium (amigel), and/or cellulose and mixtures thereof. Natural powders may include clay, diatomaceous earth, fuller's earth, silica, silica shells or spherical silica, fumed silica, spherical silica, hydrated silica, silica silylate, mica, titanated mica, talc, cellulose or spherical cellulose beads, microcrystalline cellulose, corn starch, rice starch, glyceryl starch, soy flour, walnut shell powder, agar, sericite, dextran, nylon, silk powder, chalk, calcium carbonate, bismuth oxychloride, iron oxide, titanium dioxide, aluminum silicate, magnesium aluminum silicate, calcium silicate, magnesium trisilicate, aluminum starch octenylsuccinate, bentonite, hectorite, kaolin, maltodextrin, montmorillonite, zinc laurate, zinc myristate, zinc rosinate, alumina, attapulgite, tin oxide, titanium hydroxide, trimagnesium phosphate, or mixtures thereof. Synthetic thickeners may include, for example, AMP isostearoyl hydrolyzed collagen, AMP isostearoyl hydrolyzed wheat protein, cetyl hydroxyethylcellulose, chondroitin sulfate, cocoamidopropyldimethylamine C8-16 isoalkysuccinyl lactoglobulin sulfonate, cocodimonium hydroxypropyl hydrolyzed collagen, distarch phosphate, ethyl ester of hydrolyzed animal protein, guar hydroxypropyltrimonium chloride, hydrolyzed animal or plant protein, hydroxypropyl guar, hydroxypropylmethyl cellulose, hydroxypropyl cellulose, isostearoyl hydrolyzed collagen, methylcellulose, nitrocellulose, nonoxynyl hydroxyethylcellulose, acrylate polymers, acrylamine polymers, acrylic acid polymers (carbomer), PVMIMA Decadiene crosspolymers, polyvinylpyrrolidone polymers, silicone oils, polyethylene thickeners, aluminum starch octenyl succinate, trihydroxystearin, and mixtures thereof. Other natural and synthetic thickeners may be found in the Cosmetic Handbook and CTFA ingredient inform.

As used herein, the term "ursolic acid" refers to a pentacyclic triterpene acid having as CAS accession number 77-52-1.

As used herein, "vitamin" refers to an organic compound required as a vital nutrient in tiny amounts by an organism, i.e. an organic chemical compound (or related set of compounds) is called a vitamin when it cannot be synthesized in sufficient quantities by an organism, and must be obtained from the diet. Examples of vitamins include, but are not limited to, vitamin A, vitamin B, such as vitamin B3 (niacinamide), vitamin B5, and vitamin B12, vitamin C, vitamin K, vitamin F and different forms of vitamin E like alpha, beta, gamma or delta tocopherols or their mixtures, and derivatives thereof.

As used herein, the term "wound" relates to a body lesion with a discontinuity of the normal integrity of the tissue structures. The term intends to also encompass the terms "sore", "lesion", "necrosis" and "ulcer". Normally, the term "sore" is a popular term for almost any lesion of the skin or of the mucosa membranes and the term "ulcer" is a local defect or excavation of the surface of an organ or tissue, produced by the detachment of the necrotic tissue. Lesion generally relates to any tissue defect. Necrosis relates to the dead tissue due to infection, lesion, inflammation or infarctions.

The term "zync pyrithione", as used herein, refers to bis(2-pyridylthio)zinc 1,1'-dioxide, which is a coordination complex of zinc having antifungal and anti-bacterial effect.

Cosmetic Compositions

The results obtained from the 64-gene array analysis using keratinocyte progenitors from human skin biopsies treated with/without magnetosomes revealed an ability of magnetosomes to favour the stem cell state of the epidermal progenitors (translated as an increase in the expression of the stem cell marker Keratin 19) and to simultaneously reduce the levels of production of key specific markers of differentiated (aged) cells (Keratin 1, Keratin 10 and Filaggrin)—those which reside within the uppermost layers of the skin—. This study shows that magnetosomes induce and preserve an undifferentiated, more proliferative, "young" state of human epidermal keratinocytes which is complemented by the inhibition of the expression of specific markers of epidermal differentiation or aging This "pro-stemness", "anti-differentiating" effect of magnetosomes in human epidermal keratinocytes opens the possibility for their use in cosmetic or skin care compositions. The conclusion we extract from this study is that these magnetosomes (MS) have a "retinoid-like" effect on the epidermal cells of the skin nonetheless exempt from the harmful secondary effects associated to retinoid compounds when they are topically applied onto the skin.

Therefore, in a first aspect, the invention relates to a cosmetic or skin care composition comprising magnetosomes and a cosmetically acceptable adjuvant, wherein the magnetosomes are isolated from a magnetotactic microorganism and wherein the cosmetically acceptable adjuvant is selected from the group consisting of fillers, UVA and/or UVB sunscreens, thixotropic agents, antioxidants, dyes, pigments, fragrances, thickeners, vitamins, moisturizers, and nonionic or amphoteric polymers.

The sizes or mean sizes of the magnetosomes may vary depending in particular on the method used for their preparation. In a preferred embodiment, the magnetosomes are monodomain nanoparticles (i.e. they possess only one magnetic domain) with sizes lower than about 1 µm, in general lower than about 500 nm, lower than about 300 nm, preferably between about 10 nm and about 120 nm, preferably between about 10 nm and about 70 nm, most probably between about 30 nm and about 50 nm. Preferably, the size of the magnetic nanoparticles is expressed as the mean diameter of the particles, expressed in nm, resulting from the analysis of at least two, typically of at least ten, preferably of at least 20, and particularly preferably of at least 50 individual nanoparticles.

In specific embodiments, the size of the magnetic nanoparticles according to the invention is 35 nm to 120 nm in diameter. However, it may also be possible to produce smaller and larger particles as well. In preferred embodiments, the size of the magnetic nanoparticles produced is 45 nm to 110 nm in diameter, for example particles having a size of 55-100 nm, 65-90 nm, 75-80 nm. In other preferred embodiments, the size of the magnetic nanoparticles is greater than 50 nm in diameter, for example at least 52 nm, at least 55 nm, at least 60 nm, at least 65 nm or at least 70 nm.

The sizes of the particles forming part of the composition may differ slightly within given limits depending on the method used for their preparation. In specific embodiments of the invention, the size of at least 50 percent, preferably of at least 80 percent, and particularly preferably of at least 90 percent of the magnetic nanoparticles produced (in a single assay) is within the range given by the mean diameter plus minus 15 percent, preferably by the mean diameter plus minus 10 percent, and particularly preferably by the mean diameter plus minus 5 percent.

The magnetic nanoparticles forming part of the magnetosomes may be formed by any material which allows the nanoparticle to move in response to being placed in an appropriate magnetic field. This term is meant to also include ferromagnetic, paramagnetic and diamagnetic materials. Non-limiting suitable examples can include, $Fe_2O_3$, $Fe_3O_4$, $Fe_2O_4$, $Fe_xPt_y$, $Co_xPt_y$, $MnFe_xO_y$, $CoFe_xO_y$, $NiFe_xO_y$, $CuFe_xO_y$, $ZaFe_xO_y$, and $CdFe_xO_y$, wherein x and y vary between 1 and 6, depending on the method of synthesis known in the art. In a preferred embodiment, the magnetic nanoparticiles are iron oxide nanoparticles made of magnetite ($Fe_3O_4$), iron sulfide ($Fe_3S_4$) or mixtures thereof. The magnetite found in the magnetosomes can become oxidized to maghemite after extraction from the bacteria. Therefore, in another embodiment, the magnetosomes may contain mixtures of magnetite and maghemite.

The magnetosomes are obtained from magnetotactic microorganisms using methods known to the skilled person such as those described in U.S. Pat. Nos. 4,385,119 and 6,251,365; Heyen, U. and Schuler, D. (2003) Appl. Microbial. Biotechnol. 61, 536-544). The isolation of the magnetic particles from the host cells may comprise additional processing steps such as a selection of particular fractions of particles based on their magnetic properties, for example by applying to the particles magnetic fields of different field strengths.

In a more preferred embodiment, the magnetotactic microorganisms are magnetotactic bacteria. In a yet more preferred embodiment, the magnetotactic bacteria is selected from the group consisting of *Magnetospirillum magneticum* strain AMB-1, magnetotactic coccus strain MC-1, three facultative anaerobic vibrios strains MV-1, MV-2 and MV-4, the *Magnetospirillum magnetotacticum* strain MS-1, the *Magnetospirillum gryphiswaldense* strain MSR-1, a facultative anerobic magnetotactic spirillum, *Magnetospirillum magneticum* strain MGT-1, and an obligate anaerobe, *Desulfovibrio magneticus* RS-1. These magnetosomes are characterized in that the membrane which surrounds the magnetosomes derives from the microorganism from where they have been isolated. Moreover, magnetosomes derived from magnetotactic microorganisms also contain different proteins derived from the microorganism which are associated to the membrane. Moreover, the magnetosome is enriched in a specific set of proteins. Therefore, the protein profile of the magnetosomes isolated from a magnetotactic bacteria is specific from the microorganism and contains a set of proteins which differ from the set of membrane proteins.

In a preferred embodiment, the magnetosomes have been isolated from *Magnetospirillum (M.) gryphiswaldense* strain MSR-1.

In one embodiment, the magnetosomes forming part of the composition may form chains. These chains of magnetosomes contain preferably between 2 and 30 magnetosomes, typically between 4 and 20 magnetosomes. Most of the magnetosomes belonging to these chains possess crystallographic directions and preferably also easy axes orientated in the direction of the chain elongation, which is usually [1:11]. Consequently, the chains of magnetosomes possess a magnetic anisotropy, which is stronger than that of individual magnetosomes. As a result, strong aggregation of the chains of magnetosomes is prevented. When several chains of magnetosomes containing typically between 4 and 20 magnetosomes interact, it results in the formation of a longer chain of magnetosomes, containing typically more than 4 to 20 magnetosomes. The length of a chain of magnetosomes is preferably less than 1200 nm, more preferably less than 600 nm, most preferably less than 300 nm. The arrangement in chains of the magnetosomes results in that the magnetosomes are not prone to aggregation and also possess a stable magnetic moment. The arrangement in chains of the magnetosomes also provides an interaction with the eukaryotic cells, which is advantageous due to their low level of aggregation.

In an embodiment, the magnetosomes belonging to the chain are surrounded by a biological membrane. The magnetosomes may be bound to each other via a biological filament whose structure is only partly known according to A. Komeili, Ann. Rev. Biochem. 2007, 76, 351-366.

The magnetosome size distribution can vary quite significantly depending on the bacterial strain and bacterial growth conditions.

In one embodiment, the magnetotactic bacteria are cultivated in a growth medium containing the standard growth medium of magnetotactic bacteria and an additive, which is a transition metal, such as for example Cobalt, Nickel, Copper, Zinc, Manganese, Chrome or a mixture of two or more of these metals. In an embodiment, the doping of the magnetosomes with a transition metal, e.g. cobalt, is carried out by adding about 0.02 µM to 1 mM, preferably 0.02 µM to 200 µM, preferably 1 µM to 100 µM, preferably 2 to 20 µM solution of transition metal (e.g. cobalt) within the growth medium of the magnetotactic bacteria. The magnetotactic bacteria synthesized in the presence of cobalt, e.g. cobalt quinate, or another transition metal possess improved magnetic properties even when the percentage of cobalt doping is lower than 2 percent (S. Staniland et al., Nature Nanotech., 2008, 3, 158-162). For chemically synthesized nanoparticles, a percentage of co-doping larger than about 10 percent is usually necessary to observe large changes in the magnetic properties (A. Franco et al., J. Mag. Mag. Mat, 2008, 320, 709-713; R. Tackett et al., J. Mag. Mag Mat, 2008, 320, 2755-2759).

In another embodiment, the magnetotactic bacteria are cultivated in the presence of a chelating agent. Without being fully explained by theory, it is thought that the chelating agent binds the cations derived from iron or any one of the other transition metals used as additives, and consequently improves the penetration of iron and/or of another transition metal within the magnetotactic bacteria. In another embodiment, the chelating agent is a molecule, which contains one or several alcohol functional groups, such as catechol or their derivatives or one or several amino-alcohol functional groups, such as dopamine, deferiprone, deferoxamine, desferrioxamine, or one or several amino-carboxylic acid or ketone functional groups, such as doxorubicine, caffeine, D-penicillamine, pyrroloquinoline, HEIDA (hydroxyethylimino-N,N-diethanoic acid).

In one embodiment, the chelating agent is a molecule, which contains a phosphonate or a phosphonic acid functional group, such as AEPN (2-Aminoethylphosphonic acid), AMP (Amino-tris-(methylene-phosphonic acid)), ATMP (Amino tris(methylene phosphonic acid)), CEPA (2-carboxyethyl phosphonic acid), DMMP (Dimethyl methylphosphonate), DTPMP (Diethylenetriamine penta(methylene phosphonic acid)), EDTMP (Ethylenediamine tetra(methylene phosphonic acid)), H EDP (1-Hydroxy Ethylidene-1,1-Diphosphonic Acid), HDTMP (Hexamethylenediamine tetra(methylene phosphonic acid)), HPAA (2-Hydroxyphosphonocarboxylic acid), PBTC (Phosphonobutane-tricarboxylic acid), PMIDA (N-(phosphonomethyl)iminodiacetic acid), TDTMP (Tetramethylenediamine tetra (methylene phosphonic acid)), ADP (adenosinediphosphoric acid) or 1-{12-[4-(dipyrrometheneboron difluoride)butanoyl]amino}dodecanoyl-2-hydroxy-sn-glycero-3-phosphate, a sodium salt L-a-phosphatidic acid, a sodium salt 1-palmitoyl-2-(dipyrrometheneboron difluoride)undecanoyl-sn-glycero-3-phospho-L-serine).

In another embodiment, the chelating agent is a molecule, which contains a bis, tris or tetra-phosphonate, or a bis, tris ortetra-phosphonic acid functional group, such as a 1-hydroxymethylene-bis-phosphonic acid, propane triphosphonic acid, (nitilotris(methylene))trisphophonic acid, (phosphinylidynetris(methylene))trisphosphonic acid. Examples of 1-hydroxymethylene-bis-phosphonic acids include alendronic acid (Fosamax®), pamidronic acid, zoledronic acid, risedronic acid, neridronic acid, ibandronic acid (Bondronat®), minodronic acid and other compounds described in the literature (L. Wilder et al, J. Med. Chem., 2002, 45, 3721-3728; M. Neves, N. Med. Biol., 2002, 29, 329-338; H. Shinoda et al, Calcif. Tissue Int., 1983, 35, 87-89; M. A. Merrel, Eur. J. Phramacol., 2007, 570, 27-37). For 0.4 micro ? or 4 micro ? neridronic acid, alendronic acid and residronic acid introduced in the bacterial growth medium, it has been observed herein that the percentage of magnetosomes larger than 45 nm becomes larger than for the magnetosomes synthesized in the absence of bisphosphonic acid. Chains of magnetosomes synthesized in these conditions consequently possess improved heating properties.

In another embodiment, the chelating agent is a molecule, which contains a sulfonate or sulfonic acid functional group or BAL (Dimercaprol) such as BPDS (bathophenanthrolinedisulfonate or 4,7-di(4-phenylsulfonate)-1,10-phenanthroline), DMPS (Dimercapto-propoane sulfonate or 2,3-dimercapto-1-propanesulfonic acid), sulforhodamine 101, DMSA (Dimercatptosuccinic acid).

Other examples of chelating agents are polydentate ligands for example hemoglobin, chlorophyll, porphyrin and organic compounds containing pyrolic rings.

In another embodiment, the magnetotactic bacteria are cultivated in a growth medium, which contains both a chelating agent and a transition metal.

The percentage (w/w) of magnetosomes in the cosmetic composition according to the invention is from 0.000001 and 10 percent in weight, preferably between 0.0001 and 1 percent in weight, and more preferably between 0.001 and 0.1 percent in weight, preferably between 0.01 to 20 percent by weight, more preferably from 0.2 to 10 percent by weight and better still from 0.5 to 2 percent by weight, with respect to the total weight of the composition. In a preferred embodiment, the percentage (w/w) of magnetosomes in the composition is about 0.000001% to 0.001%.

In a preferred embodiment, the compositions according to the invention comprise at least one additional cosmetically active or skin care agent. Suitable skin care agents that can form part of the compositions according to the invention include, without limitation, antioxidants, free-radical scavengers, antimicrobial agents, anti-acne agents, reducing agents, vitamins, skin protecting agents, skin bleaching agents, skin conditioning agents, skin soothing agents, skin healing agents, collagen promoters, exfoliators, self tanners, chelators, hair removers, anti-erythema agents, anti-redness agents, anti-rosacea agents, depuffing agents, anti-edema agents, anti-swelling agents, green tea extract, *P. emblica* (Amla), *arnica*, chamomile extract, cucumber extract, skin protecting agents, skin conditioning agents, antioxidants, collagen promoters, soluble collagen, self tanner and mixtures thereof, antiwrinkle agents, anti-skin-atrophy agents and mixtures thereof.

The cosmetic composition according to the invention contains a cosmetically acceptable adjuvant is selected from the group consisting of fillers, UVA and/or UVB sunscreens, thixotropic agents, antioxidants, preserving agents, dyes, pigments, fragrances, thickeners, vitamins, hormones, moisturizers, wetting agents, anionic, nonionic or amphoteric polymers and dermatological active substances.

The compositions according to the present invention may be presented in any solid, liquid or semi-solid formulation, for example and not restricted to, creams, multiple emulsions, for example and not restricted to, oil and/or silicone in water emulsions, water-in-oil and/or silicone emulsions, water/oil/water or water/silicone/water type emulsions, and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols, including leave-on and rinse-off formulations. These formulations can be incorporated by techniques known by the people skilled in the art into different types of solid accessories, for example and not restricted to, bandages, gauzes, t-shirts, socks, tights, underwear, girdles, gloves, diapers, sanitary napkins, dressings, bedspreads, wipes, adhesive patches, non-adhesive patches, microelectric patches or face masks, or can be incorporated into different make-up products such as make-up foundation, for example fluid foundations and compact foundations, make-up removal lotions, make-up removal milks, under-eye concealers, eye shadows, lipsticks, lip protectors, lip gloss and powders, among others.

Cosmetic Methods

The authors of the present invention have found that compositions of the present invention are useful for stimulating cellular growth, stimulating stem-cell activation and growth in skin tissues. This effect can be achieved in the absence of an external magnetic field. Such increased cell growth can help regulate or rejuvenate mammalian skin tissues. Thus, in another aspect, the invention relates to a cosmetic method for skin care in a subject which comprises the topical administration to said subject of a composition comprising magnetic nanoparticles which are forming part of a magnetosome and wherein said method is carried out in the absence of a magnetic field (the nanoparticles have not been placed in a magnetic field prior to administration and/or wherein the nanoparticles are not subjected to a magnetic field after application), and wherein the magnetosomes are isolated from a magnetotactic microorganism.

The term "in the absence of a magnetic field", as used herein, refers to a method wherein the nanoparticles have not been placed in a magnetic field prior to administration and wherein the subject is not subjected to a magnetic field in the region of application of the nanoparticles after application. The term "magnetic field" is used herein to denote an externally applied magnetic field which is different from the earth's own magnetic field.

Suitable nanoparticles for use in the cosmetic method of the invention include nanoparticles formed by any material as described above in the context of the cosmetic compositions of the invention.

In specific embodiments, the size of the magnetic nanoparticles according to the invention is 20 nm to 150 nm in diameter. However, it may also be possible to produce smaller and larger particles as well. In preferred embodiments, the size of the magnetic nanoparticles produced is 25 nm to 50 nm in diameter, for example particles having a size of 25-30 nm, 30-35 nm, 35-40 nm, 40-45 nm or 45-50 nm. In other preferred embodiments, the size of the magnetic nanoparticles is greater than 50 nm in diameter, for example at least 52 nm, at least 55 nm, at least 60 nm, at least 65 nm or at least 70 nm.

The magnetic nanoparticles form part of magnetosomes which have been isolated from a magnetotactic microorganism. In a preferred embodiment, the magnetotactic microorganism is a magnetotactic bacteria. In yet another embodiment, the magnetotactic bacteria is selected from the group consisting of *Magnetospirillum gryphiswaldense* MSR-1, *Magnetospirillum magneticum* AMB-1, *Magnetospirillum magnetotacticum* MS-1, *Magnetospirillum magneticum* strain MGT-1, magnetotactic coccus strain MC-1, *Desulfovibrio magneticus* RS-1 and anaerobic vibrios strains MV-1, MV-2 and MV-4.

The magnetosomes for use in the cosmetic methods according to the invention can also be formulated as a cosmetic or skin care composition and, in particular, any of the compositions mentioned in the section "Cosmetic compositions" can be used in the method according to the present invention.

The enhancement of the epidermal stem cell population promoted by topical treatment with magnetosomes has a direct positive impact in the renewal and regeneration capabilities of the skin, providing a visible rejuvenation effect. This is complemented by the ability of the magnetosomes to diminish the aging rate of keratinocytes and keratinocyte progenitors throughout the epidermal layers. The combination of these two actions results in a slowed down chronological aging of the skin and significant rejuvenation effect. Therefore, in a particular embodiment of the invention, the compositions of the invention are used for the prevention and treatment of chronological aging.

In another embodiment, the cosmetic compositions according to the invention are used for the treatment or prevention of photoaging. In a similar fashion to the above mentioned effect on the prevention and treatment of chronological aging, photoaging of the skin may be partially reversed by topical treatment with MS due to the promotion of an increased renewal of the skin thanks to the augmented levels of epidermal stem cells and the loss of the useless outermost layers of photoaged keratinocytes.

In another embodiment, the cosmetic methods according to the invention are suitable for the treatment or prevention of lipofuscin accumulation (yellow-brown stains on the skin's surface). Lipofuscin is composed of lipid, debris and protein residues of lysosomal digestion which accumulate into granules that acquire a characteristic yellow-brown color. The accumulation of lipofuscin granules is associated with skin aging, giving rise to visible yellowish spots on the skin's surface. One of the main proteins that accumulate within lipofuscin granules is Filaggrin. Therefore, regular topical treatment according to the invention—which trigger a reduction in the amount of Filaggrin in the outermost epidermal layers—may constitute an efficient way of preventing lipofuscin yellowish spots.

In another embodiment, the cosmetic methods of the invention are useful for the treatment or as aid in the treatment or prevention of skin pigmentation disorders (i.e. melasma). The topical treatment of the skin with the methods according to the invention prevents the excessive thickening of the stratum corneum, *granulosum* and *spinosum*. These results in a reduction of the amount of any kind of pigment accumulation that may be entrapped into the outermost layers of the skin and therefore MS topical treatment may induce an efficient reduction of the intensity and even number of pigment spots.

In additional embodiments, the compositions according to the invention are useful for improving the condition and aesthetic appearance of skin affected by aging, particularly matured or maturing skin, by anyone of the following methods: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; ameliorating the effects of estrogen imbalance; preventing and/or treating skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation; thickening skin tissue (i.e., building the epidermis and/or dermis layers of the skin and where applicable the keratinous layers of the nail and hair shaft), preventing and/or retarding atrophy of mammalian skin, preventing and/or retarding the appearance of spider vessels and/or red blotchiness on mammalian skin, preventing and/or retarding the appearance of dark circles under the eye of a mammal, preventing and/or retarding sallow-colored mammalian skin, preventing and/or retarding sagging of mammalian skin, softening and/or smoothing lips, hair and nails of a mammal, preventing and/or relieving itch of mammalian skin, regulating skin texture (e.g. wrinkles and fine lines), and improving skin color (e.g. redness, freckles) and any combinations thereof.

The percentage (w/w) of magnetic nanoparticles in the cosmetic composition for use in the cosmetic method according to the invention is from 0.00001 and 50 percent in weight, preferably between 0.0001 and 40 percent in weight, and more preferably between 0.001 and 30 percent in weight, preferably between 0.1 to 20 percent by weight, more preferably from 0.2 to 10 percent by weight and better still from 0.5 to 2 percent by weight, with respect to the total weight of the composition.

In a preferred embodiment, the cosmetic method of the invention is carried out by the topical application of a composition comprising magnetic nanoparticles and at least one additional cosmetically active or skin care agent. Suitable cosmetically active and skin care agents have been described above in the context of the compositions of the invention.

In another preferred embodiment, the cosmetically acceptable adjuvant is selected from the group consisting of fillers, UVA and/or UVB sunscreens, thixotropic agents, antioxidants, preserving agents, dyes, pigments, fragrances, thickeners, vitamins, hormones, moisturizers, wetting agents, anionic, nonionic or amphoteric polymers and dermatological active substances.

In another embodiment, the method of the present invention is characterized by the quantity of magnetosomes used during the cosmetic treatment. This quantity of magnetosomes is related to the quantity of iron oxide contained in the suspension of chains of magnetosomes. This quantity is estimated by measuring the amount of iron oxide present in the suspension of chains of magnetosomes, which is administered. It lies between about 0.001 mg and about 100 mg of iron oxide, preferably between about 0.01 mg and about 100 mg of iron oxide, more preferably between about 0.01 mg and about 10 mg of iron oxide, more preferably between 0.1 and 10 mg of iron oxide, After applying the composition to the skin, it can be left on the skin for a period of at least about 15 minutes, or at least about 30 minutes, or at least about 1 hour, or for at least several hours or, for example, at least about 12 hours.

Compositions of the present invention may be topically applied to mammalian skin that is in need of treatment for one or more signs of skin aging as described above. In one embodiment, the compositions are applied to skin in need of treatment for lines and wrinkles and/or loss of elasticity. The compositions may be applied to the skin in need of such treatment according to a suitable treatment regimen, e.g., every month, every week, every other day, every day, twice a day, or the like.

Any part of the external portion of the face, hair, and/or nails can be treated, e.g., face, lips, gums, under-eye area, eyelids, scalp, neck, torso, arms, hands, legs, feet, fingernails, toenails, scalp hair, eyelashes, eyebrows, etc. The composition can be applied with the fingers or with an implement or device (e.g., pad, cotton ball, applicator pen, spray applicator, dental applicator and the like).

Another approach to ensure a continuous exposure of the skin to at least a minimum level of the beneficial compositions of the invention is to apply the composition in a patch, for example, to selected tissues such as the face. Such an approach is particularly useful for problem skin areas needing more intensive treatment (e.g., a wound, facial crows feet area, frown lines, under eye area, onto the gums and the like). The patch can be occlusive, semi-occlusive or non-occlusive and can be adhesive or non-adhesive. The composition can be contained within the patch or be applied to the skin prior to application of the patch. In a typical application the patch is preferably left on the skin for a period of at least about 5 minutes, or at least about 15 minutes, or at least about 30 minutes, or at least about 1 hour, or at night as a form of night therapy.

In certain embodiments, compositions of the present invention may also be useful for treating other need states associated with skin. For example, compositions of the present invention may be useful for treating post-inflammatory hyperpigmentation, for reducing pore size, for reducing sebum production, and for scar mitigation. In certain other embodiments, compositions of the present invention may be applied simultaneously with or within several hours of a mechanical or physical exfoliant such as a microdermabrasion treatment, or with a chemical exfoliant or keratolytic agent such as salicylic acid. In certain other embodiments, compositions of the present invention are applied to mucosa or other tissue such as vaginal, oral, or ocular tissue. In certain other embodiments, compositions of the present invention are applied to mild wounds or post-surgical sites to facilitate healing, to insect bites, to poison ivy or similar skin conditions, or in general to mitigate itch.

Therapeutic Methods

Since magnetosomes regulate the levels of expression of genes involved in the process of keratinization of the skin, the potential therapeutic applications of this active may be targeted to alleviate the symptoms of skin disorders which involve an abnormal keratinization process, specifically those where there is a significant increase in the differentiated or aged epidermal keratinocyte populations that form the uppermost layers of the skin (spinous and granular layers), what is also known as hyperkeratosis.

Thus, in another aspect, the invention relates to a composition comprising magnetic nanoparticles for use in a method for treatment of a disease which is associated with increased proliferation or accumulation of differentiating keratinocytes or of a disease which requires increased numbers/proliferation of keratinocyte progenitors or for wound healing, wherein the magnetic particles are forming part of a magnetosome and wherein the magnetosomes are isolated from a magnetotactic microorganism.

In another aspect, the invention relates to the use of a magnetic nanoparticle for the manufacture of a medicament for the treatment of a disease which is associated with increased proliferation or accumulation of differentiating keratinocytes or of a disease which requires increased numbers/proliferation of keratinocyte progenitors or for wound healing, wherein the magnetic particles are forming part of a magnetosome and wherein the magnetosomes are isolated from a magnetotactic microorganism.

In another aspect, the invention relates to a method for the treatment of a disease which is associated with increased proliferation or accumulation of differentiating keratinocytes, of a disease which requires increased numbers/proliferation of keratinocyte progenitors or for wound healing in a subject in need thereof which comprises the administration to said subject of a magnetic nanoparticle, wherein the magnetic particles are forming part of a magnetosome and wherein the magnetosomes are isolated from a magnetotactic microorganism.

Suitable magnetic nanoparticles forming part of magnetosomes for use in the therapeutic method of the invention include nanoparticles formed by any material as described above in the context of the cosmetic compositions of the invention.

In specific embodiments, the size of the magnetic nanoparticles according to the invention is 20 nm to 150 nm in diameter. However, it may also be possible to produce smaller and larger particles as well. In preferred embodiments, the size of the magnetic nanoparticles produced is 25 nm to 50 nm in diameter, for example particles having a size of 25-30 nm, 30-35 nm, 35-40 nm, 40-45 nm or 45-50 nm. In other preferred embodiments, the size of the magnetic nanoparticles is greater than 50 nm in diameter, for example at least 52 nm, at least 55 nm, at least 60 nm, at least 65 nm or at least 70 nm.

The magnetosomes are isolated from a magnetotactic microorganism. In a preferred embodiment, the magnetotactic microorganism is a magnetotactic bacteria. In yet another embodiment, the magnetotactic bacteria is selected from the group consisting of *Magnetospirillum gryphiswaldense* MSR-1, *Magnetospirillum magneticum* AMB-1, *Magnetospirillum magnetotacticum* MS-1, *Magnetospirillum magneticum* strain MGT-1, magnetotactic coccus strain MC-1, *Desulfovibrio magneticus* RS-1 and anaerobic vibrios strains MV-1, MV-2 and MV-4.

In a preferred embodiment, the composition comprising magnetic nanoparticles is used for the treatment of eczema, in particular when this is accompanied by hyperkeratinization of skin areas.

In another embodiment, the compositions comprising magnetic nanoparticles are useful for the treatment of ichthyosis. In particular, since the magnetic nanoparticles according to the invention lead to a reduction of the levels of filaggrin and in view of the presence of abnormal filaggrin that causes ichthyosis *vulgaris*, the magnetic nanoparticles according to the invention are useful in the treatment of ichthyosis *vulgaris*. Moreover, since the topical administration of the magnetic nanoparticles results in a reduction of the expression of keratin 1 and keratin 10 and in view of the fact that epidermolytic ichthyosis and keratinopathic ichthyosis disease is associated to the presence of abnormal keratin 1 and keratin 10 in the uppermost layers of the skin, the magnetic nanoparticles according to the invention are also particularly useful in the treatment of epidermolytic ichthyosis and keratinopathic ichthyosis diseases. In addition, since the topical administration of the magnetic nanoparticles results in a reduction of the expression of keratin 1 and in view of the fact that Ichthyosis *hystrix* is associated to the presence of abnormal keratin 1 in the uppermost layers of the skin, the magnetic nanoparticles according to the invention are also particularly useful in the treatment of ichthyosis *hystrix*.

In another embodiment, the magnetic nanoparticles are used for the treatment of hyperkeratosis and, in particular, palmoplantar keratodermas, including focal acral hyperkeratosis (late onset keratoderma) and plantar hyperkeratosis, papulosquamous hyperkeratosis including including drug-induced keratoderma, granular parakeratosis (or axillary granular parakeratosis) or keratosis *punctata* of the palmar creases, follicular hyperkeratosis (or phrynoderma) (since this disease is caused by overproduction of keratin inside the hair follicles with plugged follicles full of protein, sebum, debris and associated inflammation as a result, magnetic nanoparticles would help unclog the affected follicles) and hyperkeratosis of the nipple and aureola.

The term "follicular hyperkeratosis" is used herein indistinctly with the term phrynoderma and is used to refer to an hereditary common mild In another embodiment, the invention relates to a method for the treatment of plaque psoriasis.

In another embodiment, the invention relates to a method for the treatment of papulopostular rosacea. Papulopustular rosacea is one of the main types of rosacea (which is a type of dermatosis) and can be easily mistaken for acne since it is characterized by the presence of papule and pustule lesions with a red apparance. There is no cure for rosacea and the current treatments are aimed to keep the condition under control. Its evolution greatly depends on the specific features of each individual's skin. Because of all this factors the key to minimize rosacea symptoms is to maintain a constant topical and/or oral treatment. In individuals with papulopustular rosacea, it would be useful to keep the papules and pustules at their lowest even trying to prevent their development, which could be achieved with topical application of magnetic nanoparticles.

In another embodiment, the invention relates to a method for the treatment of disorders in the proliferation of keratinocytes from the uppermost layers of the skin that lead to hyperkeratinized benign or malign tumors including, actinic keratosis (since differentiated keratinocyte populations— those which express Keratin 1, 10 and Filaggrin—is the main cell population appearing in actinic keratosis lesions, magnetic nanoparticles might aid in these cases due to their ability to favor the basal keratinocyte population by promotion of Keratin 19 expression, hence reducing as well the hyperkeratinization of the skin in these areas and minimizing the risk of developing a carcinoma), squamous cell carcinoma and paraneoplastic keratoderma.

In another embodiment, the invention relates to a method for the treatment of skin pigmentation disorders and, in particular, melasma.

In another embodiment, the invention relates to a method for the treatment of acne. Since keratinization is one of the aggravating factors underlying acne disorders, mainly given that it contributes to the clogging of the acne-affected pores, the ability of the magnetic nanoparticles according to their invention to halt an excessive keratinization of the skin makes them suitable agente for the treatment of acne. In particular, the complementary topical treatment with creams or lotions containing magnetic nanoparticles according to the invention would help to improve these skin conditions from inside by preventing an excessive production of normal or aberrant keratin instead of just trying to dissolve the thickened cornified layers using chemicals (i.e. urea, salicylic acid, α-hydroxy acids etc.) or enzymatic (i.e. proteolytic) treatments from the outside. The magnetic nanoparticles may be used in combination with certain vitamins (such as topical and/or oral vitamin A or retinoids, vitamin E, B complex vitamins and/or vitamin C) and topical lipids rich in essential fatty acids (such as vitamin F, composed by omega 3 and omega 6 fatty acids) in order to improve the overall regime's result.

In another embodiment, the invention relates to a method for the treatment of any skin conditions where there is a lack or slowed rate of skin renewal due to depleted epidermal stem cell populations but there is a need to avoid any kind of excessive keratinization resulting from the stem cell stimulation.

In another embodiment, the therapeutic methods of the invention comprise the treatment of wounds since magnetosomes would boost the regeneration of the skin avoiding excessive keratinization and/or scarring.

The term "wound" used in the present context means any wound (see below for a classification of wounds) and in any particular phase of the healing process, including the phase before having started any healing or even before a specific wound is produced, such as a surgical incision (prophylactic treatment). Wounds are typically classified in one of four stages depending on the depth of the wound. Thus, stage I wounds are those limited to the epithelium, stage II wounds are those extending to the dermis, stage III wounds are those extending to the subcutaneous tissue and stage IV wounds are those in which the bone is exposed.

Examples of wounds which can be prevented and/or treated according to the present invention are, for example, open wounds and closed wounds. Open wounds which can be treated with the compositions of the invention include, but are not limited to, burns caused cold or heat, incisions, ulcers, lacerations, abrasions, acne, bite wounds, punctures or gunshot wounds or closed wounds such as contusions or hematomas, lesions of the blood and lymphatic vessels such as Buerger's disease, lymphedema and ulcus cruris, post-surgery wounds such as wounds after a skin transplant and sutured wounds, decubitus ulcer, pressure ulcer, diabetic ulcer, post-herpetic ulcers and lesions by irradiation. Closed wounds which can be treated with the compositions of the invention include, but are not limited to, contusions or hematomas.

Aseptic wounds, contused wounds, incised wounds, lacerated wounds, non-penetrating wounds (i.e., wounds in which there is no discontinuity of the skin, but there is lesion in the underlying structures), open wounds, penetrating wounds, perforating wounds, punctured wounds, septic wounds, subcutaneous wounds, etc can also be treated according to the present invention. Examples of sores are decubitus ulcers, aphthae, chrome ulcers, cold ulcers, pressure ulcers, etc. Examples of ulcers are, for example, peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucosal ulcer, symptomatic ulcer, trophic ulcer, tropical ulcer and venereal ulcer, for example caused by gonorrhea (including urethritis, endocervicitis and proctitis). The conditions related to wounds or sores which can be successfully treated according to the invention are burns, anthrax, tetanus, gaseous gangrene, scarlatina, erysipelas, sycosis barbae, folliculitis, impetigo contagiosa or bullous impetigo, etc. There is frequently an overlapping between the use of the terms "wound" and "ulcer" and "wound" and "sore" and, moreover, the terms are often used randomly. Therefore, as has been previously mentioned, in the present context the term "wound" includes the terms "ulcer", "lesion", "sore" and "infarction" and the terms are used indistinctly unless otherwise indicated.

The types of wounds to be treated according to the invention also include i) general wounds, such as, for example, surgical, traumatic, infectious, ischemic, thermal, chemical and bullous wounds; ii) specific wounds of the oral cavity, such as, for example, wounds after extractions, endodontic wounds especially in relation to the treatment of cysts and abscesses, ulcers and bacterial, viral or autoimmune lesions, mechanical, chemical, thermal, infectious and lichenoid wounds; herpetic ulcers, aphthous stomatitis, acute necrotizing ulcerative gingivitis and burning mouth syndrome are specific examples; and iii) wounds on the skin, such as, for example, neoplasias, burns (for example, chemical or thermal burns), lesions (bacterial, viral, autoimmune), bite wounds and surgical incisions. Another way to classify the wounds is as i) small loss of tissue due to surgical incisions, minor abrasions and minor bite wounds, or as ii) significant loss of tissue. This latter group includes ischemic ulcers, pressure sores, fistulas, lacerations, severe bite wounds, thermal burns and wounds in donor site (in soft and hard tissues) and infarctions.

Another type of wounds that can be treated according to the invention include diabetic foot wounds, caused by the disease of the arteries that irrigate the foot and often complicated by periferic nerve damage and infection, that can produce injuries, ulcers and atrophy of skin and gangrene.

Another further type of wounds treatable by the invention are varicose ulcer wounds, that are a type of venous ulcer characterized by the loss of continuity of the skin on a region with varicose conditions that can appear after a simple trauma.

In a preferred embodiment the composition of the invention is used for the treatment of a wound in which the wound is selected from the group consisting of an aseptic wound, a contused wound, an incised wound, a lacerated wound, a non-penetrating wound, an open wound, a penetrating wound, a perforating wound, a punctured wound, a septic wound, a subcutaneous wound, an ischemic ulcer, a pressure ulcer, a fistula, a bite wound, a thermal burn wound, a diabetic foot wound and a donor site wound.

In another preferred embodiment, the extract or the pharmaceutical composition of the invention are used for the healing of a wound wherein the wound is selected from the group consisting of an aseptic wound, a contused wound, an incised wound, a lacerated wound, a non-penetrating wound, an open wound, a penetrating wound, a perforating wound, a punctured wound, a septic wound, a subcutaneous wound, an ischemic ulcer, a pressure sore, a fistula, a bite wound, a thermal burn, a donor site wound, a diabetic foot wound and a varicose ulcer wound.

As used in the present invention "healing" of a wound refers to the physiological process in which the wounded (damaged) area returns to its normal state. If it refers to an open wound, the healing refers to the process by which the skin or mucosa again forms a continuous barrier by means of the increase of connective tissue and of epithelial cells. The person skilled in the art will appreciate that, after the healing, the wounded area can comprise scar tissue which is not identical to the surrounding tissue. The use of the compositions of the invention extract can prevent or reduce the formation of scar or reduce the unpleasant appearance of the scar tissue formed during the process of healing.

In some embodiments, the therapeutic composition can be added to suitable contact layer dressings, including, for example, thin, non-adherent sheets placed on an area to protect tissue from for example, direct contact with other agents or dressings applied to the treatment site. In some embodiments, contact layers can be deployed to conform to the shape of the area of the skin treatment site and are porous to allow the skin augmentation composition to pass through for absorption onto the skin treatment site.

Elastic Bandages: suitable elastic bandages can include dressings that stretch and conform to the body contours. In certain embodiment, the fabric composition can include for example, cotton, polyester, rayon or nylon. In certain other embodiments, the elastic bandage can for example, provide absorption as a second layer or dressing, to hold a cover in place, to apply pressure or to cushion a treatment site.

Foams: suitable foam dressings can include sheets and other shapes of foamed polymer solutions (including polyurethane) with small, open cells capable of holding liquid solution of the skin augmentation composition. Exemplary foams can be for example, impregnated or layered in combination with other materials. In certain embodiment, the absorption capability can be adjusted based on the thickness and composition of the foam. In certain other embodiments, the area in contact with the treatment site can be non-adhesive for easy removal. In yet another embodiment, the foam can be used in combination with an adhesive border and/or a transparent film coating that can serve as an anti-infective barrier.

Gauzes Non-Woven dressings: suitable gauze dressings and woven dressings can include, dry woven or non-woven sponges and wraps with varying degrees of absorbency. Exemplary fabric composition can include cotton, polyester or rayon. In certain embodiments, gauzes and non-woven dressing can be available sterile or non-sterile in bulk and with or without an adhesive border. Exemplary gauze dressings and woven dressings can be used for moderate to slow release of the skin augmentation composition and covering a variety of wound treatment sites.

Hydrogels (Amorphous): suitable amorphous hydrogel dressings can include formulations of water, polymers and other ingredients with no shape, designed to donate moisture and to maintain a moist healing environments and or to rehydrate the skin treatment site while concomitantly releasing a therapeutically effective amount of the skin augmentation composition. In some embodiments, hydrogels can be used in combination with a secondary dressing cover.

Hydrogel Impregnated Dressings: suitable impregnated hydrogel dressings can include gauzes and non-woven sponges, ropes and strips saturated with an amorphous hydrogel. Amorphous hydrogels can include for example, formulations of water, polymers and other ingredients with no shape, designed to donate moisture to a dry treatment site and to maintain a moist healing environment while concomitantly releasing a therapeutically effective amount of the skin augmentation composition.

Hydrogel Sheets: suitable hydrogel sheets can include for example, three-dimensional networks of cross-linked hydrophilic polymers that are insoluble in water and interact with aqueous solutions by swelling. Exemplary hydrogels are highly conformable and permeable and can release varying amounts of the skin augmentation composition depending on their composition. In some embodiments, the hydrogel is non-adhesive against the skin treatment site or treated for easy removal. The released rate of the skin augmentation composition from the hydrogel can be adjusted depending on the chemical affinity of the hydrogel for the composition. Generally, the released composition provides an amount of each active agent in the range of about 0.01 mg/cm$^2$ to about 10 mg/cm$^2$ of skin treated.

Cosmetic Compositions Targeted in Magnetosomes and Uses Thereof

The magnetosomes can incorporate a cosmetically active agent. When the magnetosomes are exposed to a magnetic field, heat is generated which results in the release of the cosmetically active agent from magnetosomes. Thus, in another aspect, the invention relates to a cosmetic or skin care composition comprising magnetosomes and a cosmetically acceptable adjuvant wherein the magnetosomes contain an effective amount of at least a cosmetically active agent which is bound to the magnetosomes or incorporated into the magnetosomes, wherein the magnetosomes are isolated from a magnetotactic microorganism.

In one embodiment, the cosmetically active agent can be incorporated into the magnetosomes. Magnetosomes comprising a cosmetically active agent incorporated within the magnetosomes can be obtained by lipidation of nanomagnetic particles in the presence of the active component, leading to the incorporation of the active component within the lipid bilayer. A general discussion of techniques for preparation of liposomes and of medication encapsulating liposomes can be found in U.S. Pat. No. 4,224,179 (Schneider). See, also Mayer et al., Chemistry and Physics of Lipids, 40: 333-345 (1986). See also, U.S. Pat. No. 6,083,539 for the encapsulation of an active agent dry powder composition. For incorporation of active agents into nanoparticles, see, e.g., M. M. de Villiers et al. (editors), Nanotechnology in Drug Delivery, (2009) American Associate of Pharmaceutical Scientists. For incorporation of active agents into micelles, see, e.g., D. R. Lu and S. Oie, Cellular Drug Delivery: Principles and Practice, (2004) Humana Press Inc. Totowa, N.J. Relipidation can be carried out using any defined lipid mixture or any phospholipid blend. In a preferred embodiment, the magnetosomes are lipidated using a phopsholipid mixture as defined above in the context of the cosmetic compositons of the invention.

In another embodiment, the cosmetically active agent can be conjugated to, associated to or embedded in the magnetic nanoparticles or the magnetosomes. Conjugation techniques generally result in the formation of one or more covalent bonds between the cosmetically active agent and the magnetosome while association techniques generally utilize one or more of hydrophobic, electrostatic or van der Waals interactions. In another embodiment, the cosmetically active agent is embedded in the magnetic nanoparticle or in the magnetosome.

A variety of techniques may be used for conjugating or associating a cosmetically active agent to a magnetosome. For example, where the cosmetically active agent is a peptide or polypeptide, the peptide is conjugated to the magnetic particles using techniques known in the art such as Cu-catalyzed azide/alkyne[3+2] cycloaddition "Click Chemistry" as described by Rostovtsev et al. (2002) Angew. Chem. Int. Ed. 41: 2596-2599 and Tornoe et al. (2002)/. Org. Chem. 67: 3057-3064; azide/DIFO (Difluorinated Cyclooctyne) Cu-free Click Chemistry as described by Baskin et al. (2007) PNAS Vol. 104, No. 43: 167393-16797; azide/phosphine "Staudinger Reaction" as described by Lin et al. (2005)/. Am. Chem. Soc. 127: 2686-2695; azide/triarylphosphine "Modified Staudinger Reaction" as described by Saxon and Bertozzi (2000) Mar. 17 Science 287(5460): 2007-10; and catalyzed olefin cross metathesis reactions as described by Casey (2006)/. of Chem. Edu. Vol. 83, No. 2: 192-195, Lynn et al. (2000)/. Am. Chem. Soc. 122: 6601-6609, and Chen et al. (2003) Progress in Chemistry 15: 401-408.

Where the cosmetically active agent is a low molecular weight compound or small molecule, a variety of techniques may be utilized to conjugate the low molecular weight compound or small molecule to a magnetic nanoparticle as described herein, e.g., Click chemistry as described in Loh et al., Chem Commun (Camb), 2010 Nov. 28; 46(44):8407-9. Epub 2010 Oct. 7. See also, Thomson S., Methods Mol Med., {2004); 94:255-65, describing conjugation of small molecule carboxyl, hydroxyl, and amine residues to amine and sulfhydryl residues on proteins.

Methods are also available in the art for conjugating cosmetically active agents to magnetosomes. See, for example, G. Gregoriadis (editor), Liposome Technology Third Edition, Volume II Entrapment of Drugs and Other materials into Liposomes, (2007), Informa Healthcare, New York, N.Y., which describes techniques for coupling peptides to the surface of liposomes. For the covalent attachment of proteins, to liposomes see, New, R.C.C., Liposomes: A Practical Approach, (1990) Oxford University Press Inc., N.Y. at pages 163-182.

In an embodiment, the cosmetically active agent is selected from the group consisting of anti-acne agents, shine control agents, anti-inflammatory agents, sunscreens, photoprotectors, antioxidants, keratolytic agents, surfactants, moisturizers, vitamins, energy enhancers, emollients, lubricants, anti-perspiration agents, astringents, deodorants, anti-callous agents, nucleotides, allantoin, betaine, maslinic acid, ursolic acid, growth factors, oligo or polysaccharides, amino acids, peptides, glycerin, retinol, alpha-hydroxyacids, beta-hydroxyacids, an extract of *Aloe Vera*, benzoyl peroxide, zinc pyritione and agents for hair and/or skin conditioning.

The magnetosomes are isolated from a magnetotactic microorganism. In another embodiment, the magnetotactic microorganism is a magnetotactic bacteria. In yet another embodiment, the magnetotactic bacteria is selected from the group consisting of *Magnetospirillum gryphiswaldense* MSR-1, *Magnetospirillum magneticum* AMB-1, *Magnetospirillum magnetotacticum* MS-1, *Magnetospirillum magneticum* strain MGT-1, magnetotactic coccus strain MC-1, *Desulfovibrio magneticus* RS-1 and anaerobic vibrios strains MV-1, MV-2 and MV-4. I In one embodiment, the nanomagnetic particles have a diameter of from about 35 nm to about 120 nm. In yet another embodiment, the cosmetic or skin care composition contains a percentage (w/w) of magnetosomes from about 0.000001% to about 0.001%.

In another aspect, the invention relates to a cosmetic method for skin care in a subject comprising the topical administration to said subject of the cosmetic or skin care composition according to the invention and applying a magnetic field under conditions adequate for the release of the cosmetically active agent from the magnetosomes.

In one embodiment, the alternative magnetic field applied during the treatment is characterized by a frequency lying between about 50 kHz and about 1000 kHz, preferably between about 100 kHz and about 500 kHz, more preferably between about 100 kHz and about 200 kHz. In another embodiment, the magnetic field is characterized by a strength lying between about 0.1 mT and about 200 mT, preferably between about 1 mT and about 100 mT, more preferably between about 10 mT and about 60 mT, typically between about 10 mT and about 50 mT. In another embodiment, the magnetic field is applied during a time period varied between 1 second and 6 hours.

The maximum value of the magnetic field strength is determined by the value at which it becomes toxic for the organism (i. e. essentially when it generates Foucault's currents) or in which the increase in temperature results in the inactivation of the cosmetically active agent. It may be possible that magnetic fields of strengths higher than 200 mT can be used if they are shown to be non-toxic.

In another embodiment, the method of the present invention is characterized by the frequency of the magnetic field which is applied. In a preferred embodiment, the frequency of a magnetic field is between 50 and 1000 kHz.

In another embodiment, the method of the present invention is characterized by the length of time during which the magnetic field is applied. This length of time may be between about 1 second and about 6 hours, preferably between about 1 minute and about 1 hour, preferably between 0.5 and 30 minutes, most preferably between 1 minute and 30 minutes.

Additional Aspects of the Invention

1. A cosmetic or skin care composition comprising magnetosomes and a cosmetically acceptable adjuvant.

2. The cosmetic or skin care composition according to aspect 1 wherein the magnetosomes are isolated from a magnetotactic microorganism.

3. The cosmetic or skin care composition according to aspect 2 wherein the magnetotactic microorganism is a magnetotactic bacteria.

4. The cosmetic or skin care composition according to aspect 3 wherein the magnetotactic bacteria is selected from the group consisting of *Magnetospirillum gryphiswaldense* MSR-1, *Magnetospirillum magneticum* AMB-1, *Magnetospirillum magnetotacticum* MS-1, *Magnetospirillum magneticum* strain MGT-1, magnetotactic coccus strain MC-1, *Desulfovibrio magneticus* RS-1 and anaerobic vibrios strains MV-1, MV-2 and MV-4.

5. The cosmetic or skin care composition according to any of aspects 1 to 4 wherein the nanomagnetic particles have a diameter of from about 35 nm to about 120 nm 6. The cosmetic or skin care composition according to any of aspects 1 to 5 wherein the percentage (w/w) of magnetosomes in the composition is from about 0.000001% to about 0.001%.

7. The cosmetic or skin care composition according to any of aspects 1 to 6 further comprising at least one additional cosmetically active or skin care agent.

8. The cosmetic or skin care composition according to any of aspects 1 to 7 wherein the cosmetically active or skin care agent is selected from the group consisting an anti-acne agent, a shine control agent, an anti-inflammatory agent (non-NFκB Inhibiting), a sunscreen, a photoprotector, an antioxidant, a keratolytic agent, a surfactant, a moisturizer, a vitamin, an energy enhancer, an emollient, a lubricant, an anti-perspiration agent, an astringent, a deodorant, an anti-callous agent, an agent for hair and/or skin conditioning, a nucleotide, an hormone, allantoin, betaine, maslinic acid, ursolic acid, a growth factors, an oligosaccharide, a polysaccharide, an amino acid, a peptide, glycerin, retinol, an alpha-hydroxyacid, a beta-hydroxyacid, an extract of *Aloe Vera*, benzoyl peroxide, zinc pyritione and an agent for hair and/or skin conditioning.

9. The cosmetic composition according to any of aspects 1 to 8 wherein the cosmetically acceptable adjuvant is selected from the group consisting of fillers, UVA and/or UVB sunscreens, thixotropic agents, antioxidants, preserving agents, dyes, pigments, fragrances, thickeners, vitamins, moisturizers, wetting agents, anionic, nonionic or amphoteric polymers.

10. A cosmetic method for skin care in a subject which comprises the topical administration to said subject of a composition comprising magnetic nanoparticles, wherein the nanoparticles have not been placed in a magnetic field prior to administration and/or wherein the nanoparticles are not subjected to a magnetic field after application.

11. A cosmetic method according to aspect 10 for the prevention or treatment of chronological aging, photoaging, the accumulation of lipofuscin or skin pigmentation disorders.

12. The cosmetic method according to aspects 10 or 11 wherein the magnetic particles are forming part of a magnetosome.

13. The cosmetic method according to aspect 12 wherein the magnetosomes are isolated from a magnetotactic microorganism.

14. The cosmetic method according to aspect 13 wherein the magnetotactic microorganism is a magnetotactic bacteria.

15. The cosmetic method according to aspect 14 wherein the magnetotactic bacteria is selected from the group consisting of *Magnetospirillum gryphiswaldense* MSR-1, *Magneto-

*spirillum magneticum* AMB-1, *Magnetospirillum magnetotacticum* MS-1, *Magnetospirillum magneticum* strain MGT-1, magnetotactic coccus strain MC-1, *Desulfovibrio magneticus* RS-1 and anaerobic vibrios strains MV-1, MV-2 and MV-4.

16. The cosmetic method according to any of aspects 10 to 15 wherein the nanomagnetic particles have a diameter of from about 35 nm to 120 nm.

17. The cosmetic method according to any of aspects 10 to 16 wherein the percentage (w/w) of magnetic particles in the composition is from about 0.000001% to about 0.001%.

18. The cosmetic method according to any of aspects 10 to 17 wherein the composition comprising magnetic particles further comprises at least one additional skin care agent.

19. The cosmetic method according to aspect 18 wherein the additional skin care agent is selected from the group consisting of vitamin A, vitamin E and collagen.

20. The cosmetic method according to any of aspects 10 to 19 wherein the cosmetically acceptable adjuvant is selected from the group consisting of fillers, UVA and/or UVB sunscreens, thixotropic agents, antioxidants, preserving agents, dyes, pigments, fragrances, thickeners, vitamins, hormones, moisturizers, wetting agents, anionic, nonionic or amphoteric polymers and dermatological active substances.

21. A composition comprising magnetic nanoparticles for use in the treatment of a disease which is associated with decreased proliferation of keratinoyctes, of a disease which requires increased proliferation of keratinocytes or for wound healing.

22. A composition according to claim 21 wherein the disease which requires increased proliferation of keratinocytes is selected from the group consisting of eczema, ichthyosis, hyperkeratosis, plaque psoriasis, papulopostular rosacea, hyperkeratinized tumors, melisma and acne.

23. The composition for use according to aspects 21 or 22 wherein the magnetic particles are forming part of a magnetosome.

24. The composition for use according to aspect 23 wherein the magnetosomes are isolated from a magnetotactic microorganism.

25. The composition for use according to aspect 24 wherein the magnetotactic microorganism is a magnetotactic bacteria.

26. The composition for use according to aspect 25 wherein the magnetotactic bacteria is selected from the group consisting of *Magnetospirillum gryphiswaldense* MSR-1, *Magnetospirillum magneticum* AMB-1, *Magnetospirillum magnetotacticum* MS-1, *Magnetospirillum magneticum* strain MGT-1, magnetotactic coccus strain MC-1, *Desulfovibrio magneticus* RS-1 and anaerobic vibrios strains MV-1, MV-2 and MV-4.

27. The composition for use according to any of aspects 22 to 26 wherein the nanomagnetic particles have a diameter of from about 35 nm to 120 nm.

28. The composition for use according to any of aspects 22 to 27 wherein the percentage (w/w) of magnetic particles in the composition is from about 0.000001% to about 0.001%.

29. A cosmetic or skin care composition comprising magnetosomes and a cosmetically acceptable adjuvant wherein the magnetosomes contain an effective amount of at least a cosmetically active agent which is bound to the magnetosomes or incorporated into the magnetosomes.

30. A cosmetic or skin care composition according to aspect 29 wherein the cosmetically active agent is selected from the group consisting of an anti-acne agent, a shine control agent, an anti-inflammatory agent (non-NFκB Inhibiting), a sunscreen, a photoprotector, an antioxidant, a keratolytic agent, a surfactant, a moisturizer, a vitamin, an energy enhancer, an emollient, a lubricant, an anti-perspiration agent, an astringent, a deodorant, an anti-callous agent, an agent for hair and/or skin conditioning, a nucleotide, allantoin, betaine, maslinic acid, ursolic acid, a growth factors, an oligosaccharide, a polysaccharide, an amino acid, a peptide, glycerin, retinol, an alpha-hydroxyacid, a beta-hydroxyacid, an extract of *Aloe Vera*, benzoyl peroxide, zinc pyritione and an agent for hair and/or skin conditioning.

31. The cosmetic or skin care composition according to aspect 30 wherein the magnetosomes are isolated from a magnetotactic microorganism.

32. The cosmetic or skin care composition according to aspect 31 wherein the magnetotactic microorganism is a magnetotactic bacteria.

33. The cosmetic or skin care composition according to aspect 32 wherein the magnetotactic bacteria is selected from the group consisting of *Magnetospirillum gryphiswaldense* MSR-1, *Magnetospirillum magneticum* AMB-1, *Magnetospirillum magnetotacticum* MS-1, *Magnetospirillum magneticum* strain MGT-1, magnetotactic coccus strain MC-1, *Desulfovibrio magneticus* RS-1 and anaerobic vibrios strains MV-1, MV-2 and MV-4.

34. The cosmetic or skin care composition according to any of aspects 30 to 33 wherein the nanomagnetic particles have a diameter of from about 35 nm to about 120 nm 35. The cosmetic or skin care composition according to any of aspects 30 to 34 wherein the percentage (w/w) of magnetosomes in the composition is from about 0.000001% to about 0.001%.

36. A cosmetic method for skin care in a subject comprising the topical administration to said subject of the cosmetic or skin care composition according to any of aspects 29 to 35 and applying a magnetic field under conditions adequate for the release of the cosmetically active agent from the magnetosomes.

37. A cosmetic method according to aspect 36 wherein the amplitude of the magnetic field is lying between about 0.1 and 200 mT.

38. A cosmetic method according to aspects 36 or 37 wherein the frequency of a magnetic field is between 50 and 1000 kHz.

39. A cosmetic method according to any of aspects 36 to 38 wherein the magnetic field is applied during a time period varied between 1 second and 6 hours.

The invention is described herein by way of the following examples which are merely illustrative and not limitative of the scope of the invention.

EXAMPLES

Materials and Methods

Cell Type and Culture and Assay Conditions

Normal human epidermal keratinocytes enriched in proliferative keratinocytes (KSC) isolated from an otoplasty on an 8 year-old female donor, used at the 2nd passage.

Cells were cultured at 37° C. and 5% $CO_2$ in Keratinocyte-SFM supplemented with Epidermal Growth Factor (EGF) 0.25 ng/ml, Pituitary extract (PE) 25 µg/ml and Gentamycin 25 µg/ml. Cells were assayed in keratinocyte-SFM supplemented with Gentamycin 25 µg/ml.

Isolation of Magnetosomes from *Magnetospirillum gryphiswaldense* (Strain MSR-1)

Magnetosomes were isolated essentially as described in U.S. Pat. No. 6,251,365 B1.

Cytotoxicity Assay

10000 KSC/well, used at the 3$^{rd}$ passage were incubated for 48 h in assay medium. After treatment, the cells were incubated with MTT (tetrazolium salt) reduced in blue formazan crystals by succinate dehydrogenase (mitochondrial enzyme). This transformation is proportional to the enzyme activity. After cell dissociation, formazan crystals were dissolved in DMSO. The optical density (OD) of the extracts at 540 nm, which is proportional to the number of living cells and their metabolic activity, was recorded with a microplate reader (VERSAmax, Molecular Devices).

Culture and Treatment

Keratinocytes were seeded and cultured in culture medium for 24 hours and then culture medium was replaced with assay medium for 24 hours. The medium was then replaced with assay medium containing or not (control) the test compound and cells were incubated for 48 hours. All experimental conditions were performed in n=3. After 48 hours of total incubation time, the supernatants were collected and frozen at −80"C for potential future analyses and cells were washed in phosphate buffered saline solution (PBS) and immediately frozen at −80° C.

Differential Expression Analysis

The expression of markers was analyzed using RT-qPCR method on mRNA extracted from cell monolayers for each treatment (before RNA extraction the replicates were pooled). Analysis of gene expression was performed in n=2 using a dedicated customized PCR array ("mQPA HNHEK-AX111214") dedicated to research and adapted to 'screening' format (Marker qPCR array or 'mQPA').

Reverse Transcription

Total RNA was extracted from each sample using TriPure Isolation Reagent® according to the supplier's instructions. The amount and quality of RNA were evaluated using a lab-on-a-chip Bioanalyzer (Agilent technologies). Potential contaminant traces of genomic DNA were removed using the DNAfree system (Ambion). The reverse-transcription of mRNA was conducted in presence of oligo(dT) and Superscript II reverse transcriptase. Quantification of cDNA was performed using Nanovuc (GE Healthcare) and adjustment of cDNA.

Quantitative PCR

The PCRs (Polymerase Chain Reactions) were performed using the <<LightCycler•ID®>> system (Roche Molecular System Inc.) according to supplier's instructions. This system allows rapid and powerful PCRs, after determining analysis conditions of the test primers. The reaction mix (10 µl final) was added as follows:

2.5 µl of cDNA,
primers forward and reverse,
reagent mix containing taq DNA polymerase, SYBR Green I and $MgCl_2$.

The incorporation of fluorescence in amplified DNA was measured continuously during the PCR cycles. This resulted in a "fluorescence intensity" versus "PCR cycle" plot allowing the evaluation of a relative expression (RE) value for each marker. The value selected for RE calculations is the "output point" (Ct) of the fluorescence curve. For a considered marker, the highest is the cycle number; the lowest is the mRNA quantity. The RE value was expressed in arbitrary units (AU) according to the formula:

$$(\tfrac{1}{2}^{number\ of\ cycles}) \times 10^6$$

For a standardized interpretation, the following table is used

| Relative expression (% of control) | Classification of the effects |
|---|---|
| >300% | Strong stimulation |
| >200% and <300% | Stimulation |
| >150% and <z200% | Slight stimulation, to be confirmed |
| >50% and <65% | Moderate inhibition, to be confirmed |
| >30% and <50% | Inhibition |
| <30% | Strong inhibition |

Example 1

Cytotoxicity Assay

The results are shown in Table 2.

TABLE 2

Effect of magnetosomes on the viability of keratinocytes.
+; Normal population, +/− growth reduction; −: toxicity; 0: cell mortality;
g: grains of compound; op: opacity of compound; *; morphological modification;
ag: agglutinated cells; SEM: Standard error of the mean (standard deviation divided by sample size square reel).

| | Control | | Magnetosomes (Unit: µg/ml) Stock solution: 2 mg/ml in 10 mM HEPES, 1 MM EDTA | | | | | | | |
|---|---|---|---|---|---|---|---|---|---|---|
| | | | 0.09 | 0.27 | 0.82 | 2.5 | 7.4 | 22.2 | 66.7 | 200 |
| Viability | 87 | 101 | 83 | 75 | 73 | 85 | 84 | 73 | 76 | 62 |
| | 99 | 102 | 84 | 86 | 80 | 82 | 83 | 86 | 81 | 69 |
| | 98 | 112 | 88 | 93 | 88 | 86 | 92 | 86 | 94 | 73 |
| Mean | 100 | | 85 | 85 | 80 | 84 | 86 | 83 | 84 | 68 |
| SEM | 3 | | 2 | 5 | 4 | 1 | 3 | 5 | 5 | 3 |
| Morphological observations | + | | + | + | + | + | + | +/−, g | −, g | −, g |

No appreciable cytotoxicity was observed at the concentration equal or below 7.4 micrograms per mL.

Example 2

Effect of Magnetosomes on the Gene Expression Profile

The analysis of the 64-gene array revealed some significant changes in the expression of specific genes which regulate the aging of cutaneous cells and the skin when human keratinocytes were treated with magnetosomes (see Table 3).

TABLE 3

Effect of a magnetosome composition on the expression level of a series of genes in keratinocytes.
Underlined: Up-regulated genes (arbitrary selection for stimulation: % >150); Italics: Down-regulated genes
(arbitrary selection for inhibition: %) <65. n.d. not detected.

| | mQPA H-NHEK- AX111214 | | Control Cycles | Magnetosomes - 7.4 µg/ml | | | | |
|---|---|---|---|---|---|---|---|---|
| | | | | Cycles | % Control (ACTB) | % Control (RPL13A) | % Control (GAPDH) | % Control (Mean HK) |
| Housekeeping | GAPDH | Glyceraldehyde-3-phosphate dehydrogenase | 17.78 17.73 | 17.68 17.92 | 117 | 90 | 100 | 100 100 |
| | RPL13A | Ribosomal protein L13a | 18.07 18.03 | 17.97 17.90 | 130 | 100 | 111 | 111 |
| | ACTB | Actin, beta | 18.50 18.53 | 18.78 18.78 | 100 | 77 | 86 | 85 |
| Growth factors | TNFRSF1A | Tumor necrosis factor receptor superfamily, member 1A | 24.73 25.01 | 24.76 25.44 | 105 | 81 | 90 | 89 |
| | VEGFA | Vascular endothelial growth factor A | 25.64 25.59 | 25.38 25.57 | 133 | 102 | 114 | 113 |
| | VEGFB | Vascular endothelial growth factor B | 28.80 28.81 | 28.34 28.64 | <u>150</u> | 115 | 129 | 128 |
| | VEGFC | Vascular endothelial growth factor C | 29.69 29.84 | 29.60 29.46 | 141 | 109 | 121 | 121 |
| | FGF7 | Fibroblast growth factor 7 (keratinocyte growth factor) | 27.77 28.01 | 28.40 28.51 | 81 | *62* | 69 | 69 |
| | EGF | Epidermal growth factor (beta-urogastrone) | 29.46 29.56 | 30.10 29.66 | 94 | 72 | 80 | 80 |
| | FGFR1 | Fibroblast growth factor receptor 1 | 29.87 29.78 | 29.93 29.80 | 117 | 90 | 100 | 100 |
| | EGFR | Epidermal growth factor receptor (erythroblastic leukemia viral (v-erb-b) oncogene homolog, avian) | 21.87 21.91 | 22.49 22.46 | 80 | *62* | 69 | 68 |
| | FGFR2 | Fibroblast growth factor receptor 2 | 29.21 29.13 | 29.05 29.22 | 123 | 95 | 105 | 105 |
| | TGFA | Transforming growth factor, alpha | 25.51 25.46 | 25.54 25.01 | 141 | 109 | 121 | 121 |
| | TGFB1 | Transforming growth factor, beta 1 | 27.07 27.52 | 27.13 27.28 | 127 | 97 | 108 | 108 |
| Chemokines, cytokines, cytokine receptors | CCL27 | Chemokine (C-C motif) ligand 27 | 31.14 31.23 | 31.59 31.46 | 95 | 73 | 81 | 81 |
| | CCL20 | Chemokine (C-C motif) ligand 20 | 28.01 28.12 | 27.57 27.79 | <u>157</u> | 121 | 135 | 134 |
| | CXCL1 | Chemokine (C—X—C motif) ligand 1 (melanoma growth stimulating activity, alpha) | 28.71 28.70 | 28.39 28.64 | 138 | 106 | 118 | 117 |
| | CXCR2 | chemokine (C—X—C motif) receptor 2 | 32.47 33.11 | 32.50 32.87 | 127 | 98 | 109 | 108 |
| | CCR6 | Chemokine (C-C motif) receptor 6 | 30.30 29.96 | 30.02 29.96 | 132 | 101 | 113 | 112 |
| | CCR4 | Chemokine (C-C motif) receptor 4 | 33.10 33.74 | 33.01 33.32 | 141 | 108 | 120 | 120 |
| | IL1A | Interleukin 1, alpha | 21.20 21.06 | 21.64 21.51 | 88 | 68 | 76 | 75 |
| | IL1B | Interleukin 1, beta | 20.93 20.90 | 21.08 21.08 | 107 | 82 | 92 | 91 |
| | IL8 | Interleukin 8 | 36.69 36.91 | 37.44 36.59 | 108 | 83 | 92 | 92 |
| | IL20 | Interleukin 20 | 28.71 29.15 | 29.42 29.47 | 83 | *64* | 71 | 71 |
| | TNF | Tumor necrosis factor (TNF superfamily, member 2) | 33.53 33.59 | 33.78 33.96 | 97 | 75 | 83 | 83 |
| Miscellaneous | PTGS2 | Prostaglandin-endoperoxide synthase 2 (prostaglandin G/H synthase and cyclooxygenase) | 27.46 27.50 | 26.94 27.08 | <u>167</u> | 128 | 143 | 142 |
| | CD34 | CD34 molecule | 32.49 33.49 | 33.28 33.57 | 84 | *65* | 72 | 72 |
| | DEFB4 | Defensin, beta 4 | 35.55 35.67 | 35.61 35.72 | 116 | 89 | 99 | 99 |
| | NES | Nestin | 25.61 26.23 | 25.70 25.69 | 137 | 105 | 117 | 117 |
| | TFRC | Transferrin receptor (p90, CD71) | 25.88 26.03 | 27.40 27.38 | *44* | *34* | *38* | *38* |

TABLE 3-continued

Effect of a magnetosome composition on the expression level of a series of genes in keratinocytes.
Underlined: Up-regulated genes (arbitrary selection for stimulation: % >150); Italics: Down-regulated genes
(arbitrary selection for inhibition: %) <65. n.d. not detected.

| | | | | | Magnetosomes - 7.4 µg/ml | | | |
|---|---|---|---|---|---|---|---|---|
| | mQPA H-NHEK- AX111214 | | Control Cycles | Cycles | % Control (ACTB) | % Control (RPL13A) | % Control (GAPDH) | % Control (Mean HK) |
| Cell cycle regulation - Transcription factors | BCL2L1 | apoptosis regulator bcl-x; BCL2-like 1 (BCL2L1) | 24.00 24.05 | 24.01 23.95 | 124 | 95 | 106 | 106 |
| | FOS | V-fos FBJ murine osteosarcoma viral oncogene homolog | 25.79 25.78 | 25.73 26.37 | 102 | 79 | 88 | 87 |
| Apoptosis | BAX | BCL2-associated X protein | 28.58 29.18 | 28.23 28.26 | <u>183</u> | 140 | <u>156</u> | <u>156</u> |
| | SIRT1 | Sirtuin (silent mating type information regulation 2 homolog) 1 (S. cerevisiae) | 26.69 26.78 | 26.82 27.07 | 104 | 80 | 89 | 89 |
| | CASP3 | Caspase 3, apoptosis-related cysteine peptidase | 25.53 25.44 | 25.34 25.43 | 129 | 99 | 110 | 110 |
| | CDKN2A | Cyclin-dependent kinase inhibitor 2A (melanoma, p16, inhibits CDK4) | 27.91 28.51 | 27.69 28.40 | 136 | 104 | 116 | 116 |
| | TP53 | Tumor protein p53 | 26.76 26.88 | 26.60 26.77 | 132 | 101 | 113 | 113 |
| | CDKN2Ap14 | Cyclin-dependent kinase inhibitor 2A (melanoma, p16, inhibits CDK4) | n.d. n.d. | n.d. n.d. | — | — | — | — |
| Telomere length regulation | TEP1 | telomerase-associated protein 1 | 33.66 32.77 | 31.53 31.31 | <u>399</u> | <u>307</u> | <u>341</u> | <u>340</u> |
| | POT1 | POT1 protection of telomeres 1 homolog (S. pombe) | 30.49 30.31 | 29.98 30.03 | <u>158</u> | 121 | 135 | 135 |
| Keratinocyte differentiation | KRT10 | Keratin 10 | 26.20 26.42 | 26.87 27.10 | 75 | *58* | *64* | *64* |
| | KRT1 | Keratin 1 | 27.24 27.45 | 28.44 28.77 | *50* | *39* | *43* | *43* |
| | KRT15 | Keratin 15 | 21.34 21.46 | 22.12 22.10 | 73 | *56* | *63* | *63* |
| | FLG | Filaggrin | 25.81 26.15 | 26.62 26.68 | 75 | *58* | *64* | *64* |
| | IVL | Involucrin | 25.73 25.93 | 25.99 26.08 | 104 | 80 | 89 | 89 |
| Keratinocyte proliferation | MKI67 | Antigen identified by monoclonal antibody Ki-67 | 29.70 29.74 | 29.73 29.84 | 115 | 88 | 98 | 98 |
| | KRT19 | Keratin 19 | 27.59 27.43 | 25.97 26.09 | <u>335</u> | <u>257</u> | <u>287</u> | <u>286</u> |
| Cell/cell or cell/matrix interaction | CDH1 | Cadherin 1, type 1, E-cadherin (epithelial) | 22.14 22.53 | 22.31 22.69 | 107 | 82 | 92 | 91 |
| | CTNNA1 | Catenin (cadherin-associated protein), alpha 1, 102 kDa | 25.83 26.28 | 25.94 26.11 | 121 | 93 | 104 | 104 |
| | ITGA6 | Integrin, alpha 6 | 24.65 24.57 | 24.52 24.45 | 131 | 101 | 112 | 112 |
| | ITGB1 | Integrin, beta 1 (fibronectin receptor, beta polypeptide, antigen CD29 includes MDF2, MSK12) | 20.89 20.88 | 20.90 20.83 | 122 | 94 | 104 | 104 |
| | CDSN | Corneodesmosin | 28.20 28.46 | 28.42 28.50 | 109 | 84 | 94 | 93 |
| | DSG1 | Desmoglein 1 | 27.49 27.69 | 28.41 28.58 | *64* | *49* | *55* | *55* |
| | DSP | Desmoplakin | 20.62 20.33 | 21.16 21.12 | 75 | *58* | *65* | *64* |
| | EVPL | Envoplakin | 30.09 30.47 | 30.31 30.62 | 105 | 81 | 90 | 90 |
| | ITGAV | Integrin, alpha V (vitronectin receptor, alpha polypeptide, antigen CD51) | 24.91 24.91 | 25.14 25.31 | 97 | 74 | 83 | 83 |
| | ITGA2 | Integrin, alpha 2 (CD49B, alpha 2 subunit of VLA-2 antigen CD51) receptor) | 26.12 26.12 | 25.96 26.14 | 126 | 97 | 108 | 108 |

Treatment of epidermal keratinocytes with the magnetosome preparation tested at 7.4 µg/ml, mainly induced a decreased expression of markers involved in keratinocyte differentiation (KRT10, KRT1, KRT15 and FLG), cell/cell interactions (DSG1, DSP) and an increased expression of genes involved in the proliferation (KRT19) or apoptosis (BAX). In addition, a decrease of TFRC expression, gene encoding a protein involved in iron-transport and over-expressed during keratinocyte differentiation, was also observed. For the other genes analyzed, no clear effects were shown.

Thus, a "pro-stemness", "anti-differentiating" effect of magnetosomes in human epidermal keratinocytes has been identified, supported also by the undetectable levels of the senescence marker p16INK4A found in the magnetosomes-treated keratinocytes. Therefore, it can concluded that magnetosomes have a "retinoid-like" effect in the skin, nonetheless exempt from the harmful effects associated to retinoids.

The invention claimed is:

1. A cosmetic method for skin care in a subject which comprises the topical administration to said subject of a composition comprising magnetic nanoparticles which are forming part of a magnetosome, wherein the nanoparticles are not subjected to a magnetic field after application, wherein the magnetosomes are isolated from a magnetotactic microorganism and wherein the percentage (w/w) of magnetic particles in the composition is from about 0.0001% to about 0.001%.

2. The cosmetic method according to claim 1 for the treatment of chronological aging, photoaging, the accumulation of lipofuscin or skin pigmentation disorders.

3. The cosmetic method according to claim 2 wherein the magnetotactic microorganism is a magnetotactic bacteria.

4. The cosmetic method according to claim 3 wherein the magnetotactic bacteria is selected from the group consisting of *Magnetospirillum gryphiswaldense* MSR-1, *Magnetospirillum magneticum* AMB-1, *Magnetospirillum magnetotacticum* MS-1, *Magnetospirillum magneticum* strain MGT-1, magnetotactic coccus strain MC-1, *Desulfovibrio magneticus* RS-1 and anaerobic vibrios strains MV-1, MV-2 and MV-4.

5. The cosmetic method according to claim 1 wherein the nanomagnetic particles have a diameter of from about 35 nm to 120 nm.

6. The cosmetic method according to claim 1 wherein the composition comprising magnetic particles further comprises at least one additional skin care agent.

7. The cosmetic method according to claim 6 wherein the additional skin care agent is selected from the group consisting of vitamin A, vitamin E and collagen.

8. The cosmetic method according to claim 1 wherein the cosmetically acceptable adjuvant is selected from the group consisting of fillers, UVA and/or UVB sunscreens, thixotropic agents, antioxidants, preserving agents, dyes, pigments, fragrances, thickeners, vitamins, hormones, moisturizers, wetting agents, anionic, nonionic or amphoteric polymers and dermatological active substances.

* * * * *